(12) United States Patent
Shinkai et al.

(10) Patent No.: US 9,024,053 B2
(45) Date of Patent: May 5, 2015

(54) COMPOUND OBTAINED BY DIMERIZING WITH LIGHT IRRADIATION, A COMPOUND CONTAINING A GROUP HAVING LYOPHILICITY, AND A COMPOUND CONTAINING A GROUP HAVING LIQUID-REPELLENCY

(75) Inventors: Seiji Shinkai, Fukuoka (JP); Shuichi Haraguchi, Machida (JP); Tomohiro Shiraki, Champaign, IL (US); Masashi Ogawa, Fukuoka (JP); Shuhei Nakatani, Osaka (JP); Kei Sakanoue, Fukuoka (JP); Osamu Goto, Tsukuba (JP); Hidenobu Kakimoto, Tsukuba (JP)

(73) Assignees: Joled Inc., Tokyo (JP); Sumitomo Chemical Company, Limited, Tokyo (JP)

( * ) Notice: Subject to any disclaimer, the term of this patent is extended or adjusted under 35 U.S.C. 154(b) by 307 days.

(21) Appl. No.: 13/510,207

(22) PCT Filed: Nov. 18, 2010

(86) PCT No.: PCT/JP2010/070573
§ 371 (c)(1),
(2), (4) Date: Aug. 31, 2012

(87) PCT Pub. No.: WO2011/062225
PCT Pub. Date: May 26, 2011

(65) Prior Publication Data
US 2012/0330047 A1    Dec. 27, 2012

(30) Foreign Application Priority Data

Nov. 18, 2009   (JP) .................................. 2009-263203

(51) Int. Cl.
| | | |
|---|---|---|
| C07F 7/04 | (2006.01) |
| G03F 7/027 | (2006.01) |
| C07F 7/12 | (2006.01) |
| C07F 7/18 | (2006.01) |
| G03F 7/075 | (2006.01) |
| H01L 51/00 | (2006.01) |
| G03F 7/004 | (2006.01) |

(52) U.S. Cl.
CPC . *G03F 7/027* (2013.01); *C07F 7/12* (2013.01); *C07F 7/1836* (2013.01); *G03F 7/0046* (2013.01); *G03F 7/0755* (2013.01); *H01L 51/0056* (2013.01); *H01L 51/0095* (2013.01)

(58) Field of Classification Search
USPC ........................................................ 556/441
See application file for complete search history.

(56) References Cited

U.S. PATENT DOCUMENTS

2009/0011227 A1   1/2009   Furukawa
2009/0143598 A1   6/2009   Herzog et al.

FOREIGN PATENT DOCUMENTS

| | | | |
|---|---|---|---|
| CN | 1189179 | A | 7/1998 |
| CN | 1278276 | A | 12/2000 |
| JP | 11-344804 | A | 12/1999 |
| JP | 2000-282240 | A | 10/2000 |
| JP | 2004146478 | A * | 5/2004 |
| JP | 2008-107634 | A | 5/2008 |
| JP | 2009-137845 | A | 6/2009 |
| KR | 20090008811 | A | 1/2009 |
| WO | 96/37562 | A1 | 11/1996 |
| WO | 99/23131 | A1 | 5/1999 |
| WO | 2007/102487 | A1 | 9/2007 |
| WO | 2009/118759 | A2 | 10/2009 |

OTHER PUBLICATIONS

Dawn et al., Org. Biomol. Chem., 2009, 7, 4378-4385.*
Notice of Reasons for Rejection dated Jan. 21, 2014 in corresponding Japanese Patent Application No. 2009-263203 with English translation.
Extended European Search Report dated Jun. 28, 2013 in corresponding European Patent Application No. 10831618.3.
"Norrish reaction", Jan. 1, 2013, XP055067491, Retrieved from the Internet: URL:https://en.wikipedia.org/wiki/Norrish_reaction [retrieved on Jun. 20, 2013].
A. E. Shamaev, et al., "New organosiloxanes based on 1-vinyl-2-perfluoroalkoxy-2,3,3-trifluorocyclobutanes", Russian Chemical Bulletin, International Edition, vol. 54, No. 5, May 2005, pp. 1250-1253 (XP019224663).
First Office Action issued Apr. 9, 2014 in corresponding Chinese Patent Application No. 201080052079.2 with English translation.
Office Action issued Sep. 16, 2014 in corresponding Japanese Patent Application No. 2009-263203 with English translation.
Office Action issued Dec. 3, 2014 in corresponding Taiwanese Patent Application No. 099139660 with translation.
Masaru Kimura, et al., "Detection and Thermal Properties of 1,4-Difluorobenzene-Naphthoquinone Biplanemer: a New Longicyclic π System", Tetrahedron Letters, 1992, pp. 6975-6978, vol. 33, No. 46.

(Continued)

*Primary Examiner* — Porfirio Nazario Gonzalez
*Assistant Examiner* — Kofi Adzamli
(74) *Attorney, Agent, or Firm* — Sughrue Mion, PLLC

(57) ABSTRACT

A problem of the present invention is to prevent a base layer beneath the layer to be irradiated with light from deterioration in property and a functional thin film from deterioration in property as the fine patterning of a functional film is performed with light irradiation. Means for solving the problem is a compound obtained by dimerizing with light irradiation a compound (A) containing a group that has photosensitivity and can be photodimerized and a group having lyophilicity and a compound (B) containing a group that has photosensitivity and can be photodimerized and a group having liquid-repellency.

5 Claims, No Drawings

(56) References Cited

OTHER PUBLICATIONS

Geoffrey W. Coates, et al., "Phenyl-Perfluorophenyl Stacking Interactions: Topochemical [2+2] Photodimerization and Photopolymerization of Olefinic Compounds", J. Am. Chem. Soc., 1998, pp. 3641-3649, vol. 120, No. 15.

Hans-Albert Brune, et al., "Photochemistry of fluoro- and chloro-substituted *trans*-stilbene-4-carboxylic-acids and their derivatives in the crystalline phase", J. Photochem. Photobiol. A: Chem., 1994, pp. 113-128, vol. 83, No. 2.

William J. Leigh, et al., "The photochemistry of 3,3',4,4'-tetramethoxy-and 4-hydroxy-3,3',4'trimethoxystilbene—models for stilbene chromophores in peroxide-bleached, high-yield wood pulps", Can. J. Chem., 1996, 99. 263-275, vol. 74, No. 2.

Todd Bosanac, et al., "Precipiton Reagents: Precipiton Phosphines for Solution-Phase Reductions", Organic Letters, 2004, pp. 2321-2324, vol. 6, No. 14.

Toshiki Nokami, et al., "Aqueous Photo-Dimerization Using 2-Pyridylsilyl Group as a Removable Hydrophilic Group", Chemistry Letters, 2004, pp. 596-597, vol. 33, No. 5.

The Third Office Action issued Jan. 20, 2015 in corresponding Chinese Patent Application No. 201080052079.2 with translation.

\* cited by examiner

COMPOUND OBTAINED BY DIMERIZING WITH LIGHT IRRADIATION, A COMPOUND CONTAINING A GROUP HAVING LYOPHILICITY, AND A COMPOUND CONTAINING A GROUP HAVING LIQUID-REPELLENCY

CROSS REFERENCE TO RELATED APPLICATIONS

This application is a National Stage of International Application No. PCT/JP2010/070573 filed Nov. 18, 2010, claiming priority based on Japanese Patent Application No. 2009-263203, filed Nov. 18, 2009, the contents of all of which are incorporated herein by reference in their entirety.

TECHNICAL FIELD

The present invention relates to a compound obtained by dimerizing, with light irradiation, a compound containing a group having lyophilicity, and a compound containing a group having liquid-repellency. More specifically, the present invention relates to the compound which is used as the patterning of a functional thin film is performed.

BACKGROUND ART

In the field of an organic thin film transistor device, an organic thin film solar cell, an organic EL display and the like, many functional thin films are investigated. The functional thin film is a thin film subjected to so-called fine patterning, which includes a material exhibiting various functions and is arranged at locations where the functions needs to be exhibited in a device with precision required for exhibiting the functions. Examples of the functions to be exhibited by patterning include functions of wiring, an electrode, an insulating layer, a light-emitting layer, a charge transporting layer and the like. As a technique of performing such patterning, there is, for example, a photolithography method. That is, a method for forming a functional thin film in which a thin film is formed over a surface of a substrate and the like, a layer containing a photoresist material is then formed on the thin film, and the thin film is finely patterned with the use of photosensitivity of the photoresist material. However, the functional thin film prepared with the photolithography method is likely to deteriorate highly in various functions since the steps such as UV irradiation, developing, washing and the like on the photolithography method are performed. Particularly, when the functional thin film is a functional organic thin film, functions of the functional organic thin film are likely to be highly damaged with performing the steps such as developing and washing.

As a method for solving the problem of a photolithography method, it has been proposed a method that a functional thin film is directly patterned on a substrate by using an ink-jet method, a nozzle coating method, and various roll printing methods, for example, a flexo printing or reversing. These printing methods use an ink which is usually relatively low in concentration and viscosity. Therefore, there are such methods for precisely forming a functional thin film at only the required position that a partition wall for preventing the ink from flowing is formed in a region surrounding the region where the functional thin film is formed, and that a lyophilic region which can accept the ink and a liquid-repellent region which do not accept the ink are formed on a surface of a substrate.

As the method in which a lyophilic region and a liquid-repellent region are formed on a surface of a substrate, there is known a method in which a liquid-repellent substance such as a fluorine-containing silane coupling agent is applied onto a surface of a lyophilic thin film to form a liquid-repellent thin film, a part of the liquid-repellent thin film is irradiated with light having a wavelength less than 200 nm to decompose the liquid-repellent substance, and then the decomposed product is removed. In the substrate obtained by this method, only a site irradiated with light becomes a lyophilic surface (Patent Document 1).

Further, as a method of using light having a wavelength of relatively long wavelength, there is a method in which a thin film of a liquid-repellent composition, containing a compound having a liquid-repellent group and a photopolymerization initiator, is formed on a lyophilic substrate, and a part of the thin film is irradiated with light to polymerize the liquid-repellent composition and make the composition insoluble in a solvent, and an unpolymerized portion of the composition is removed by use of a solvent to pattern a lyophilic region (Patent Document 2).

Moreover, as a method of using ultraviolet light with a relatively long wavelength, there is also known a method in which a liquid-repellent thin film containing a photocatalyst such as titanium oxide is formed on a lyophilic layer and a part of the thin film is irradiated with light to decompose the liquid-repellent thin film and to pattern a lyophilic region (Patent Document 3).

BACKGROUND ART DOCUMENTS

Patent Documents

Patent Document 1: Japanese Patent Laid-open Publication No. 2000-282240
Patent Document 2: International Publication WO 2007/102487
Patent Document 3: Japanese Patent Laid-open Publication No. H11 (1999)-344804

SUMMARY OF THE INVENTION

Problems to be Solved by the Invention

However, the method of radiating light with a wavelength less than 200 nm is a method of radiating light with high energy for a long time and requires large-scale facilities and special apparatuses such as vacuum equipment, a high-energy light source and the like, and therefore it has a problem that production cost increases. Further, the irradiation with high-energy light can deteriorate a base layer beneath the layer to be irradiated with light. Since the method of using light with a relatively long wavelength uses light with relatively low energy, it can be reduced the deterioration in property of a base layer beneath the layer to be irradiated with light. However, there is a problem that a photopolymerization initiator is contained in the liquid repellent composition, and a reaction residue of the photopolymerization initiator deteriorates a functional thin film formed thereon in property. Also, the method of using ultraviolet light with a relatively long wavelength has a problem that a photocatalyst causes the characteristics of a functional thin film formed thereon to deteriorate.

Means for Solving the Problems

That is, the present invention firstly provides a compound obtained by dimerizing, with light irradiation, a compound (A) containing a group that has photosensitivity and can be photodimerized and a group having lyophilicity and a compound (B) containing a group that has photosensitivity and can be photodimerized, and a group having liquid-repellency.

The present invention secondly provides the above compound, the compound being characterized in that the photosensitive group contained in the compound (A) contains a double bond or an aromatic fused ring.

The present invention thirdly provides the above compound, the compound being characterized in that the photosensitive group contained in the compound (B) contains a double bond or an aromatic fused ring.

The present invention fourthly provides the above compound, wherein the compound (A) is a compound represented by the formula (1-1):

[Chem. 1]

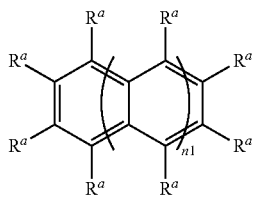

(1-1)

wherein $R^a$s independently represent a hydrogen atom or a substituent, any two adjacent $R^a$s may be coupled with each other to form a ring that is selected from among saturated hydrocarbon rings, unsaturated hydrocarbon rings, aromatic hydrocarbon rings and heterocycles and may have a substituent, at least one of the $R^a$s is a group having lyophilicity, and n1 represents an integer of 0 or more.

The present invention fifthly provides the above compound, wherein the compound (A) is a compound represented by the formula (1-2):

[Chem. 2]

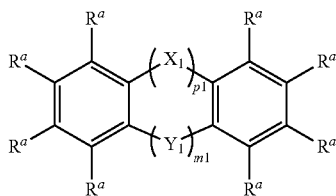

(1-2)

wherein $R^a$s independently represent a hydrogen atom or a substituent, $X_1$ and $Y_1$ may be the same or different and represent —$C(R^a)_2$—, —$N(R^a)$—, —O—, —S—, —$Si(R^a)_2$—, —$B(R^a)$— or —$C(R^a)=C(R^a)$—, any two adjacent $R^a$s may be coupled with each other to form a ring that is selected from among saturated hydrocarbon rings, unsaturated hydrocarbon rings, aromatic hydrocarbon rings and heterocycles and may have a substituent, at least one of the $R^a$s is a group having lyophilicity, and p1 and m1 are the same or different and represent an integer of 0 or more.

The present invention sixthly provides the above compound, wherein the group having lyophilicity is a group containing an atom belonging to Group 4, 5, 6, 13, 14, 15 or 16 of the periodic table.

The present invention seventhly provides the above compound, wherein the group having lyophilicity is a group containing a silicon atom.

The present invention eighthly provides the above compound, wherein the group having lyophilicity is a group represented by the formula (1-3):

[Chem. 3]

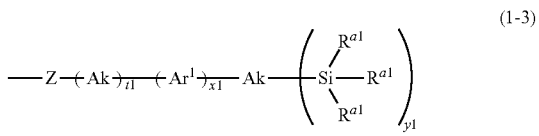

(1-3)

wherein Z represents —C(=O)O—, —OC(=O)—, —OC(=O)O—, —C(=O)—, —N($R^c$)—, —C(=O)N($R^c$)—, —N($R^c$)C(=O)—, —N($R^c$)C(=O)N($R^c$)—, -Ak-C(=O)O—, -Ak-OC(=O)—, -Ak-C(=O)O—, -Ak-C(=O)—, -Ak-N($R^c$)—, -Ak-C(=O)N($R^c$)—, -Ak-N($R^c$)C(=O)—, -Ak-N($R^c$)C(=O)N($R^c$)—, —O—, —S— or -Ak-, $Ar^1$ represents an aromatic hydrocarbon group having a valence of (1+y1) or a heterocyclic group having a valence of (1+y1), Ak represents an alkylene group having 1 to 12 carbon atoms, $R^{a1}$ represents a hydrogen atom, a halogen atom, a hydroxyl group, an alkoxy group or an alkyl group, $R^c$ represents a hydrogen atom or a substituent, and where there are a plurality of $R^c$s, these $R^c$s may be the same or different, t1 represents 0 or 1, x1 represents 0 or 1, and y1 represents an integer of 1 or more, the plurality of $R^{a1}$s may be the same or different, and where there are a plurality of Aks, these Aks may be the same or different.

The present invention ninthly provides the above compound, wherein the compound (B) is a compound represented by the formula (2-1):

[Chem. 4]

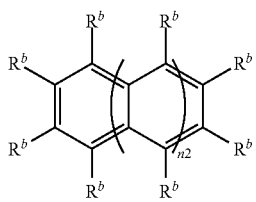

(2-1)

wherein $R^b$s independently represent a hydrogen atom or a substituent, any two adjacent $R^b$s may be coupled with each other to form a ring that is selected from among saturated hydrocarbon rings, unsaturated hydrocarbon rings, aromatic hydrocarbon rings and heterocycles and may have a substituent, at least one of the $R^b$s is a group having liquid-repellency, and n2 represents an integer of 0 or more.

The present invention tenthly provides the above compound, wherein the compound (B) is a compound represented by the formula (2-2):

[Chem. 5]

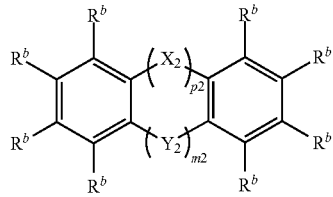

(2-2)

wherein $R^b$s independently represent a hydrogen atom or a substituent, $X_2$ and $Y_2$ may be the same or different and represent —C($R^b$)$_2$—, —N($R^b$)—, —O—, —S—, —Si($R^b$)$_2$—, —B($R^b$)— or —C($R^b$)=C($R^b$)—, any two adjacent $R^b$s may be coupled with each other to form a ring that is selected from among saturated hydrocarbon rings, unsaturated hydrocarbon rings, aromatic hydrocarbon rings and heterocycles and may have a substituent, at least one of the $R^b$s is a group having liquid-repellency, and p2 and m2 are the same or different and represent an integer of 0 or more.

The present invention eleventhly provides the compound, wherein the group having liquid-repellency is a group represented by the following formula:

[Chem. 6]

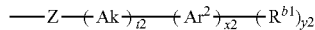

wherein Z represents —C(=O)O—, —OC(=O)—, —OC(=O)O—, —C(=O)—, —N($R^c$)—, —C(=O)N($R^c$)—, —N($R^c$)C(=O)—, —N($R^c$)C(=O)N($R^c$)—, -Ak-C(=O)O—, -Ak-OC(=O)—, -Ak-OC(=O)O—, -Ak-C(=O)—, -Ak-N($R^c$)—, -Ak-C(=O)N($R^c$)—, -Ak-N($R^c$)C(=O)—, -Ak-N($R^c$)C(=O)N($R^c$)—, —O—, —S— or -Ak-, Ak represents an alkylene group having 1 to 12 carbon atoms, $R^c$ represents a hydrogen atom or a substituent, and where there are a plurality of $R^c$s, these $R^c$s may be the same or different, $Ar^2$ represents an aromatic hydrocarbon group having a valence of (1+y2) or a heterocyclic group having a valence of (1+y2), $R^{b1}$ represents a monovalent organic group containing a fluorine atom, t2 represents 0 or 1, x2 represents 0 or 1, y2 represents an integer of 1 or more, and where there are a plurality of $R^{b1}$s, these $R^{b1}$s may be the same or different.

The present invention twelfthly provides the above compound, wherein the group having liquid-repellency is a group represented by the following formula:

[Chem. 7]

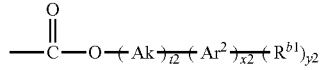

wherein $Ar^2$, $R^{b1}$, Ak, t2, x2 and y2 respectively represent the same meanings as those described above.

The present invention thirteenthly provides the above compound, wherein the group having liquid-repellency is a group represented by the following formula:

[Chem. 8]

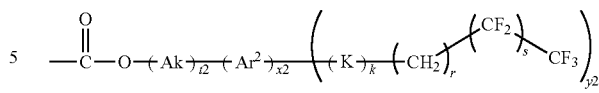

wherein $Ar^2$, Ak, t2, x2 and y2 respectively represent the same meanings as those described above, K represents —O—, —S—, —NH— or —NR—, R represents an alkyl group or an aryl group, k represents 0 or 1, r represents an integer of 0 to 6, s represents an integer of 0 to 16, and where there are a plurality of k's, these k's may be the same or different, where there are a plurality of r's, these r's may be the same or different, and where there are a plurality of s's, these s's may be the same or different.

Effects of the Invention

The compound of the present invention can be used for a process for forming a lyophilic region and a liquid repellent region on a surface of a substrate. Since the process can use light with low energy, production cost becomes low, and deterioration of the base layer beneath the layer to be irradiated with light is prevented. In addition, since the process does not use a photopolymerization initiator and a photocatalyst, deterioration of the functional thin film in property is prevented.

EMBODIMENTS FOR CARRYING OUT THE INVENTION

Explanation of Terms

Hereinafter, terms used commonly in the present specification will be described. In the present specification, the term <Cm–Cn> (m and n are each a positive integer satisfying m<n) means that the number of carbon atoms of the group described together with this term is from m to n.

The substituent refers to, unless otherwise specified, a halogen group, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a monovalent heterocyclic group, a heterocyclic thio group, an amino group, a silyl group, an acyl group, an acyloxy group, an imine residue, an amide group, an acid imide group, a carboxyl group, a hydroxyl group, an alkenyl group and an alkynyl group, shown below.

Examples of the halogen atom include a fluorine atom, a chlorine atom, a bromine atom and an iodine atom.

The alkyl group refers to unsubstituted alkyl groups and alkyl groups substituted with a halogen atom, an amino group, a mercapto group or the like, and includes both of linear alkyl groups and cyclic alkyl groups (cycloalkyl groups). The alkyl group may have a branch. The number of carbon atoms of the alkyl group is usually approximately from 1 to 20, preferably approximately from 1 to 15, and more preferably approximately from 1 to 10. Specific examples of the alkyl group include a methyl group, an ethyl group, a propyl group, an i-propyl group, a butyl group, an i-butyl group, a s-butyl group, a t-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group, a perfluorooctyl group, a trifluoropropyl group, a tridecafluoro-1,1,2,2-tetrahydrooctyl group, a heptadecafluoro-1,1,2,2-tetrahydrodecyl group, an aminopropyl group, an aminooctyl group, an aminodecyl group, a mercaptopropyl group, a mercaptooctyl group, a mercaptodecyl group and the like. Examples of C1-C12 alkyl groups include a methyl group, an ethyl group, a propyl group, an i-propyl group, a butyl group, an i-butyl group, a s-butyl group, a t-butyl group, a pentyl group, an isoamyl group, a hexyl group, a cyclohexyl group, a heptyl group, an octyl group, a nonyl group, a decyl group, a dodecyl group and the like.

The alkoxy group refers to unsubstituted alkoxy groups and alkoxy groups substituted with a halogen atom, an alkoxy group or the like, and includes both of linear alkoxy groups and cyclic alkoxy groups (cycloalkoxy groups). The alkoxy group may have a branch. The number of carbon atoms of the alkoxy group is usually approximately from 1 to 20, preferably approximately from 1 to 15, and more preferably approximately from 1 to 10. Specific examples of the alkoxy group include a methoxy group, an ethoxy group, a propyloxy group, an i-propyloxy group, a butoxy group, an i-butoxy group, a s-butoxy group, a t-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyloxy group, a perfluorooctyloxy group, a methoxymethyloxy group, a 2-methoxyethyloxy group and the like. Examples of C1-C12 alkoxy groups include a methoxy group, an ethoxy group, a propyloxy group, an i-propyloxy group, a butoxy group, an i-butoxy group, a t-butoxy group, a pentyloxy group, a hexyloxy group, a cyclohexyloxy group, a heptyloxy group, an octyloxy group, 2-ethylhexyloxy group, a nonyloxy group, a decyloxy group, a 3,7-dimethyloctyloxy group, a lauryloxy group and the like.

The alkylthio group refers to unsubstituted alkylthio groups and alkylthio groups substituted with a halogen atom or the like, and includes both of linear alkylthio groups and cyclic alkylthio groups (cycloalkylthio groups). The alkylthio group may have a branch. The number of carbon atoms of the alkylthio group is usually approximately from 1 to 20, preferably approximately from 1 to 15, and more preferably approximately from 1 to 10. Specific examples of the alkylthio group include a methylthio group, an ethylthio group, a propylthio group, an i-propylthio group, a butylthio group, an i-butylthio group, a t-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group, a trifluoromethylthio group and the like. Examples of C1-C12 alkylthio groups include a methylthio group, an ethylthio group, a propylthio group, an i-propylthio group, a butylthio group, an i-butylthio group, a s-butylthio group, a t-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and the like.

The aryl group is an atomic group obtained by excluding a hydrogen atom bonded to a carbon atom composing an aromatic ring from an aromatic hydrocarbon, and refers to unsubstituted aryl groups and aryl groups substituted with a halogen atom, an alkoxy group, an alkyl group or the like. The aryl group also includes groups having a benzene ring or a condensed ring, and groups formed by binding two or more independent benzene rings or condensed rings together with a single bond or a divalent group, for example, an alkenylene group such as a vinylene group or the like, interposed therebetween. The number of carbon atoms of the aryl group is usually approximately from 6 to 60, preferably approximately from 7 to 48, and more preferably approximately from 7 to 30. Examples of the aryl group include a phenyl group, a C1-C12 alkoxyphenyl group, a C1-C12 alkylphenyl group, a 1-naphthyl group, a 2-naphthyl group, a 1-anthracenyl group, a 2-anthracenyl group, a 9-anthracenyl group, a pentafluorophenyl group and the like, and the C1-C12 alkoxyphenyl group and the C1-C12 alkylphenyl group are preferred.

Specific examples of the C1-C12 alkoxyphenyl group include a methoxyphenyl group, an ethoxyphenyl group, a propyloxyphenyl group, an i-propyloxyphenyl group, a butoxyphenyl group, an i-butoxyphenyl group, a s-butoxyphenyl group, a t-butoxyphenyl group, a pentyloxyphenyl group, a hexyloxyphenyl group, a cyclohexyloxyphenyl group, a heptyloxyphenyl group, an octyloxyphenyl group, a 2-ethylhexyloxyphenyl group, a nonyloxyphenyl group, a decyloxyphenyl group, a 3,7-dimethyloctyloxyphenyl group, a lauryloxyphenyl group and the like.

Specific examples of the C1-C12 alkylphenyl group include a methylphenyl group, an ethylphenyl group, a dimethylphenyl group, a propylphenyl group, a mesityl group, a methylethylphenyl group, an i-propylphenyl group, a butylphenyl group, an i-butylphenyl group, a s-butylphenyl group, a t-butylphenyl group, a pentylphenyl group, an isoamylphenyl group, a hexylphenyl group, a heptylphenyl group, an octylphenyl group, a nonylphenyl group, a decylphenyl group, a dodecylphenyl group and the like.

The aryloxy group refers to unsubstituted aryloxy groups and aryloxy groups substituted with a halogen atom, an alkoxy group, an alkyl group or the like. The number of carbon atoms of the aryloxy group is usually approximately from 6 to 60, preferably approximately from 7 to 48, and more preferably approximately from 7 to 30. Specific examples of the aryloxy group include a phenoxy group, a C1-C12 alkoxyphenoxy group, a C1-C12 alkylphenoxy group, a 1-naphthyloxy group, a 2-naphthyloxy group, a pentafluorophenyloxy group and the like, and the C1-C12 alkoxyphenoxy group and the C1-C12 alkylphenoxy group are preferred.

Specific examples of the C1-C12 alkoxyphenoxy group include a methoxyphenoxy group, an ethoxyphenoxy group, a propyloxyphenoxy group, an i-propyloxyphenoxy group, a butoxyphenoxy group, an i-butoxyphenoxy group, a s-butoxyphenoxy group, a t-butoxyphenoxy group, a pentyloxyphenoxy group, a hexyloxyphenoxy group, a cyclohexyloxyphenoxy group, a heptyloxyphenoxy group, an octyloxyphenoxy group, a 2-ethylhexyloxyphenoxy group, a nonyloxyphenoxy group, a decyloxyphenoxy group, a 3,7-dimethyloctyloxyphenoxy group, a lauryloxyphenoxy group and the like.

Specific examples of the C1-C12 alkylphenoxy group include a methylphenoxy group, an ethylphenoxy group, a dimethylphenoxy group, a propylphenoxy group, a 1,3,5-trimethylphenoxy group, a methylethylphenoxy group, an i-propylphenoxy group, a butylphenoxy group, an i-butylphenoxy group, a s-butylphenoxy group, a t-butylphenoxy group, a pentylphenoxy group, an isoamylphenoxy group, a hexylphenoxy group, a heptylphenoxy group, an octylphenoxy group, a nonylphenoxy group, a decylphenoxy group, a dodecylphenoxy group and the like.

The arylthio group refers to unsubstituted arylthio groups and arylthio groups substituted with a halogen atom, an alkoxy group, an alkyl group or the like. The number of carbon atoms of the arylthio group is usually approximately from 6 to 60, preferably approximately from 7 to 48, and more preferably approximately from 7 to 30. Specific examples of the arylthio group include a phenylthio group, a C1-C12 alkoxyphenylthio group, a C1-C12 alkylphenylthio group, a 1-naphthylthio group, a 2-naphthylthio group, a pentafluorophenylthio group and the like.

The arylalkyl group refers to unsubstituted arylalkyl groups and arylalkyl groups substituted with a halogen atom, an alkoxy group, an alkyl group or the like. The number of carbon atoms of the arylalkyl group is usually approximately from 7 to 60, preferably approximately from 7 to 48, and more preferably approximately from 7 to 30. Specific examples of the arylalkyl group include a phenyl-C1-C12 alkyl group, a C1-C12 alkoxyphenyl-C1-C12 alkyl group, a C1-C12 alkylphenyl-C1-C12 alkyl group, a 1-naphthyl-C1-C12 alkyl group, a 2-naphthyl-C1-C12 alkyl group and the like.

The arylalkoxy group refers to unsubstituted arylalkoxy groups and arylalkoxy groups substituted with a halogen atom, an alkoxy group, an alkyl group or the like. The number of carbon atoms of the arylalkoxy group is usually approximately from 7 to 60, preferably approximately from 7 to 48, and more preferably approximately from 7 to 30. Specific examples of the arylalkoxy group include a phenyl-C1-C12 alkoxy group, a C1-C12 alkoxyphenyl-C1-C12 alkoxy group, a C1-C12 alkylphenyl-C1-C12 alkoxy group, a 1-naphthyl-C1-C12 alkoxy group, a 2-naphthyl-C1-C12 alkoxy group and the like.

The arylalkylthio group refers to unsubstituted arylalkylthio groups and arylalkylthio groups substituted with a halogen atom, an alkoxy group, an alkyl group or the like. The number of carbon atoms of the arylalkylthio group is usually approximately from 7 to 60, preferably approximately from 7 to 48, and more preferably approximately from 7 to 30. Specific examples of the arylalkylthio group include a phenyl-C1-C12 alkylthio group, a C1-C12 alkoxyphenyl-C1-C12 alkylthio group, a C1-C12 alkylphenyl-C1-C12 alkylthio group, a 1-naphthyl-C1-C12 alkylthio group, a 2-naphthyl-C1-C12 alkylthio group and the like.

The arylalkenyl group refers to unsubstituted arylalkenyl groups and arylalkenyl groups substituted with a halogen atom, an alkoxy group, an alkyl group or the like. The number of carbon atoms of the arylalkenyl group is usually approximately from 8 to 60, preferably approximately from 8 to 48, and more preferably approximately from 8 to 30. Specific examples of the arylalkenyl group include a phenyl-C2-C12 alkenyl group, a C1-C12-alkoxyphenyl-C2-C12 alkenyl group, a C1-C12 alkylphenyl-C2-C12 alkenyl group, a 1-naphthyl-C2-C12 alkenyl group, a 2-naphthyl-C2-C12 alkenyl group and the like, and the C1-C12 alkoxyphenyl-C2-C12 alkenyl group and the C2-C12 alkylphenyl-C2-C12 alkenyl group are preferred.

Examples of the C2-C12 alkenyl group include a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group, a 1-octenyl group and the like.

The arylalkynyl group refers to unsubstituted arylalkynyl groups and arylalkynyl groups substituted with a halogen atom, an alkoxy group, an alkyl group or the like. The number of carbon atoms of the arylalkynyl group is usually approximately from 8 to 60, preferably approximately from 8 to 48, and more preferably approximately from 8 to 30. Specific examples of the arylalkynyl group include a phenyl-C2-C12 alkynyl group, a C1-C12 alkoxyphenyl-C2-C12 alkynyl group, a C1-C12 alkylphenyl-C2-C12 alkynyl group, a 1-naphthyl-C2-C12 alkynyl group, a 2-naphthyl-C2-C12 alkynyl group and the like, and the C1-C12 alkoxyphenyl-C2-C12 alkynyl group and the C1-C12 alkylphenyl-C2-C12 alkynyl group are preferred.

Examples of the C2-C12 alkynyl group include an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group, a 1-octynyl group and the like.

The monovalent heterocyclic group refers to an atomic group obtained by excluding a hydrogen atom from a heterocyclic compound, and refers to unsubstituted monovalent heterocyclic groups and monovalent heterocyclic groups substituted with a substituent such as an alkyl group. The number of carbon atoms of the monovalent heterocyclic group is usually approximately from 3 to 60, preferably approximately from 3 to 30, and more preferably approximately from 3 to 20, excluding the number of carbon atoms of the substituent. Herein, the heterocyclic compound refers to an organic compound having a cyclic structure, which contains not only a carbon atom but also a heteroatom such as an oxygen atom, a sulfur atom, a nitrogen atom, a phosphorus atom, a boron atom, a silicon atom, a selenium atom, a tellurium atom, an arsenic atom or the like as elements composing a ring. Among the monovalent heterocyclic groups, a monovalent aromatic heterocyclic group is preferred. Examples of the monovalent heterocyclic group include a thienyl group, a C1-C12 alkylthienyl group, a pyrrolyl group, a furyl group, a pyridyl group, a C1-C12 alkylpyridyl group, a pyridazinyl group, a pyrimidyl group, a pyrazinyl group, a triazinyl group, a pyrrolidyl group, a piperidyl group, a quinolyl group, an isoquinolyl group and the like, and among these, the thienyl group, the C1-C12 alkylthienyl group, the pyridyl group and the C1-C12 alkylpyridyl group are preferred.

The heterocyclic thio group refers to groups formed by substituting a monovalent heterocyclic group for a hydrogen atom of a mercapto group. Examples of the heterocyclic thio group include heteroarylthio groups such as a pyridylthio group, a pyridazinylthio group, a pyrimidylthio group, a pyrazinylthio group, a triazinylthio group and the like.

The amino group refers to unsubstituted amino groups and substituted amino groups having one or two substituents selected from an alkyl group, an aryl group, an arylalkyl group and a monovalent heterocyclic group (hereinafter, referred to as a substituted amino group). The substituent may further have a substituent (hereinafter, sometimes referred to as a secondary substituent). The number of carbon atoms of the substituted amino group is usually approximately from 1 to 60, preferably approximately from 2 to 48, and more preferably approximately from 2 to 40, excluding the number of carbon atoms of the secondary substituent. Examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a s-butylamino group, a t-butylamino group, a pentylamino group, a hexylamino group, a heptylamino group, an octylamino group, a 2-ethylhexylamino group, a nonylamino group, a decylamino group, a 3,7-dimethyloctylamino group, a dodecylamino group, a cyclopentylamino group, a dicyclopentylamino group, a cyclohexylamino group, a dicyclohexylamino group, a ditrifluoromethylamino group, a phenylamino group, a diphenylamino group, a C1-C12 alkoxyphenylamino group, a di(C1-C12 alkoxyphenyl)amino group, a C1-C12 alkylphenylamino group, a di(C1-C12 alkylphenyl)amino group, a 1-naphthylamino group, a 2-naphthylamino group, a pentafluorophenylamino group, a pyridylamino group, a pyridazinylamino group, a pyrimidylamino group, a pyrazinylamino group, a triazinylamino group, a phenyl-C1-C12 alkylamino group, a C1-C12 alkoxyphenyl-C1-C12 alkylamino group, a di(C1-C12 alkoxyphenyl-C1-C12 alkyl)amino group, a C1-C12 alkylphenyl-C1-C12 alkylamino group, a di(C1-C12 alkylphenyl-C1-C12 alkyl)amino group, a 1-naphthyl-C1-C12 alkylamino group, a 2-naphthyl-C1-C12 alkylamino group and the like.

The silyl group refers to unsubstituted silyl groups and substituted silyl groups having one, two or three substituents selected from an alkyl group, an aryl group, an arylalkyl group and a monovalent heterocyclic group (hereinafter, referred to as a substituted silyl group). The substituent may have a secondary substituent. The number of carbon atoms of the substituted silyl group is usually approximately from 1 to 60, preferably approximately from 3 to 48, and more preferably approximately from 3 to 40, excluding the number of carbon atoms of the secondary substituent. Examples of the substituted silyl group include a trimethylsilyl group, a triethylsilyl group, a tripropylsilyl group, a tri-isopropylsilyl group, a dimethyl-isopropylsilyl group, a diethyl-isopropylsilyl group, a t-butylsilyldimethylsilyl group, a pentyldimethylsilyl group, a hexyldimethylsilyl group, a heptyldimethylsilyl group, an octyldimethylsilyl group, a 2-ethylhexyldimethylsilyl group, a nonyldimethylsilyl group, a decyldimethylsilyl group, a 3,7-dimethyloctyl-dimethylsilyl group, a dodecyldimethylsilyl group, a phenyl-C1-C12 alkylsilyl group, a C1-C12 alkoxyphenyl-C1-C12 alkylsilyl group, a C1-C12 alkylphenyl-C1-C12 alkylsilyl group, a 1-naphthyl-C1-C12 alkylsilyl group, a 2-naphthyl-C1-C12 alkylsilyl group, a phenyl-C1-C12 alkyldimethylsilyl group, a triphenylsilyl group, a tri-p-xylylsilyl group, a tribenzylsilyl group, a diphenylmethylsilyl group, a t-butyldiphenylsilyl group, a dimethylphenylsilyl group and the like.

The acyl group refers to unsubstituted acyl groups and acyl groups substituted with a halogen atom and the like. The number of carbon atoms of the acyl group is usually approximately from 1 to 20, preferably approximately from 2 to 18, and more preferably approximately from 2 to 16. Examples of the acyl group include a formyl group, an acetyl group, a propionyl group, a butyryl group, an isobutyryl group, a pivaloyl group, a benzoyl group, a trifluoroacetyl group, a pentafluorobenzoyl group and the like.

The acyloxy group refers to unsubstituted acyloxy groups and acyloxy groups substituted with a halogen atom or the like. The number of carbon atoms of the acyloxy group is usually approximately from 1 to 20, preferably approximately from 2 to 18, and more preferably approximately from 2 to 16. Examples of the acyloxy group include a formyloxy group, an acetoxy group, a propionyloxy group, a butyryloxy group, an isobutyryloxy group, a pivaloyloxy group, a benzoyloxy group, a trifluoroacetyloxy group, a pentafluorobenzoyloxy group and the like.

The imine residue refers to a residue obtained by excluding, from an imine compound having a structure represented by at least one of the formula: H—N=C< and the formula: —N=CH—, a hydrogen atom in the structure. Examples of such an imine compound include compounds formed by substituting an alkyl group, an aryl group, an arylalkyl group, an arylalkenyl group, an arylalkynyl group or the like for a hydrogen atom bonded to aldimine, ketimine or a nitrogen atom in aldimine. The number of carbon atoms of the imine residue is usually approximately from 2 to 20, preferably approximately from 2 to 18, and more preferably approximately from 2 to 16. Examples of the imine residue include a group represented by the general formula: —CR'=N—R' or the general formula: —N=C(R")$_2$ (wherein R' represents a hydrogen atom, an alkyl group, an aryl group, an arylalkyl group, an arylalkenyl group or an arylalkynyl group, R"s are the same or different and each represent an alkyl group, an aryl group, an arylalkyl group, an arylalkenyl group or an arylalkynyl group, and when two R"s are present, the two R"s may be coupled with each other to form a ring as a divalent group, for example, an alkylene group having 2 to 18 carbon atoms such as an ethylene group, a trimethylene group, a tetramethylene group, a pentamethylene group, a hexamethylene group or the like).

The amide group refers to unsubstituted amide groups and amide groups substituted with a halogen atom or the like. The number of carbon atoms of the amide group is usually approximately from 2 to 20, preferably approximately from 2 to 18, and more preferably approximately from 2 to 16. Examples of the amide group include a formamide group, an acetamide group, a propioamide group, a butyramide group, a benzamide group, a trifluoroacetamide group, a pentafluorobenzamide group, a diformamide group, a diacetamide group, a dipropioamide group, a dibutyramide group, a dibenzamide group, a ditrifluoroacetamide group, a dipentafluorobenzamide group and the like.

The acid imide group refers to a residue obtained by excluding, from an acid imide, a hydrogen atom bonded to a nitrogen atom of the acid imide. The number of carbon atoms of the acid imide group is usually approximately from 4 to 20, preferably approximately from 4 to 18, and more preferably approximately from 4 to 16.

The carboxyl group means unsubstituted carboxyl groups and substituted carboxyl groups having a substituent such as an alkyl group, an aryl group, an arylalkyl group, a monovalent heterocyclic group or the like (hereinafter, referred to as a substituted carboxyl group). The substituent may have a secondary substituent. The number of carbon atoms of the substituted carboxyl group is usually approximately from 1 to 60, preferably approximately from 2 to 48, and more preferably approximately from 2 to 45, excluding the number of carbon atoms of the secondary substituent. Examples of the substituted carboxyl group include a methoxycarbonyl group, an ethoxycarbonyl group, a propoxycarbonyl group, an isopropoxycarbonyl group, a butoxycarbonyl group, an isobutoxycarbonyl group, a s-butoxycarbonyl group, a t-butoxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethoxycarbonyl group, a pentafluoroethoxycarbonyl group, a perfluorobutoxycarbonyl group, a perfluorohexyloxycarbonyl group, a perfluorooctyloxycarbonyl group, a phenoxycarbonyl group, a naphthoxycarbonyl group a pyridyloxycarbonyl group and the like.

The aromatic hydrocarbon group having a valence of X refers to an atomic group obtained by excluding X hydrogen atoms from an aromatic hydrocarbon and includes groups having an independent benzene ring or condensed ring. The number of carbon atoms of the aromatic hydrocarbon group is usually approximately from 6 to 60, preferably approximately from 6 to 48, more preferably approximately from 6 to 30, and moreover preferably 6 to 18. The number of carbon atoms does not include the number of carbon atoms of a substituent. Specific examples of the aromatic hydrocarbon group in the case of a divalent aromatic hydrocarbon group (arylene group) include unsubstituted or substituted phenylene groups such as a 1,4-phenylene group, a 1,3-phenylene group, a 1,2-phenylene group and the like; unsubstituted or substituted naphthalenediyl groups such as a 1,4-naphthalenediyl group, a 1,5-naphthalenediyl group, a 2,6- naphthalenediyl group and the like; unsubstituted or substituted anthracenediyl groups such as a 1,4-anthracenediyl group, a 1,5-anthracenediyl group, a 2,6-anthracenediyl group, a 9,10-anthracenediyl group and the like; unsubstituted or substituted phenanthrenediyl groups such as a 2,7-phenanthrenediyl group and the like; unsubstituted or substituted naphthacenediyl groups such as a 1,7-naphthacenediyl group, a 2,8-naphthacenediyl group, a 5,12-naphthacenediyl group and the like; unsubstituted or substituted fluorenediyl groups such as a 2,7-fluorenediyl group, a 3,6-fluorenediyl group and the like; unsubstituted or substituted pyrenediyl groups such as a 1,6-pyrenediyl group, a 1,8-pyrenediyl group, a 2,7-pyrenediyl group, a 4,9-pyrenediyl group and the like; unsubstituted or substituted perylenediyl groups such as a 3,9-perylenediyl group, a 3,10-perylenediyl group and the like; and the like, and the unsubstituted or substituted phenylene groups and the unsubstituted or substituted fluorenediyl groups are preferably used.

The heterocyclic group having a valence of X refers to an atomic group obtained by excluding X hydrogen atoms from a heterocyclic compound, and the number of carbon atoms of the heterocyclic group is usually approximately from 4 to 60, preferably from 4 to 30, and particularly preferably from 6 to 12. The number of carbon atoms does not include the number of carbon atoms of a substituent. Specific examples of the heterocyclic group having a valence of X in the case of a divalent heterocyclic group include unsubstituted or substituted pyridinediyl groups such as a 2,5-pyridinediyl group, a 2,6-pyridinediyl group and the like; unsubstituted or substituted thiophenediyl groups such as a 2,5-thiophenediyl group and the like; unsubstituted or substituted furandiyl groups such as a 2,5-furandiyl group and the like; unsubstituted or substituted quinolinediyl groups such as a 2,6-quinolinediyl group and the like; unsubstituted or substituted isoquinolinediyl groups such as a 1,4-isoquinolinediyl group, a 1,5-isoquinolinediyl group and the like; unsubstituted or substituted quinoxalinediyl groups such as a 5,8-quinoxalinediyl group and the like; unsubstituted or substituted benzo[1,2,5]thiadiazolediyl groups such as a 4,7-benzo[1,2,5]thiadiazolediyl group and the like; unsubstituted or substituted benzothiazolediyl groups such as a 4,7-benzothiazolediyl group and the like; unsubstituted or substituted carbazolediyl groups such as a 2,7-carbazolediyl group, a 3,6-carbazolediyl group and the like; unsubstituted or substituted phenoxazinediyl groups such as a 3,7-phenoxazinediyl group and the like; unsubstituted or substituted phenothiazinediyl groups such as a 3,7-phenothiazinediyl group and the like; unsubstituted or substituted dibenzosilolediyl groups such as a 2,7-dibenzosilolediyl group and the like; and the like, and the unsubstituted or substituted benzo[1,2,5]thiadiazolediyl groups, the unsubstituted or substituted phenoxazinediyl groups and the unsubstituted or substituted phenothiazinediyl groups are preferably used.

As the photosensitive group, which is a group having photosensitivity and can be photodimerized, a functional group can be used without constraints as long as it absorbs light energy in a range of wavelengths from ultraviolet light to visible light to initiate a dimerization reaction. The reason why absorption of light energy is required is that photosensitivity (photofunctionality) of a compound is used when so-called fine patterning is carried out. When the light energy which the functional group absorbs is high, it is not preferred since the cost required for light irradiation is high and surrounding organic materials may be degraded by exposure to high energy. Favorable light for the functional group to absorb has a wavelength of 200 nm or more, and preferably a wavelength of 200 to 380 nm.

The dimerization referred to herein means that two molecules of an organic compound are chemically bonded with each other. The molecules to be bonded with each other may be the same or different. Chemical structures of the functional groups in the two molecules may also be the same or different. However, the structures and the combination of the functional groups preferably cause a photodimerization reaction without use of reaction aids such as a catalyst, an initiator and the like. The reason for this is that if surrounding organic materials are brought into contact with residues of the reaction aids, they may be degraded.

As these functional groups, functional groups, which have a double bond capable of a photodimerization reaction or an aromatic condensed ring having a site capable of a photodimerization reaction, are preferably used. Among these, an aromatic condensed ring group is more preferably used since it absorbs light with relatively low energy. Specific examples of the functional group preferably used include a group having a cinnamic acid ester structure, a group having a chalcone structure, a group having a styrylpyridinium structure, a group having an α-phenylmaleimide structure, an anthryl group, a group having a coumalin structure and the like.

In the present invention, the terms "a group having liquid-repellency" and "a group having lyophilicity" are used in a relative sense. The group having liquid-repellency has only to be a group which is higher in degree of the liquid-repellency than the group having lyophilicity. The group having liquid-repellency provides a thin film composed of a compound containing the group with the liquid-repellency. For example, in a thin film composed of a compound containing a group having liquid-repellency, it is preferable that contact angle of a droplet of an aqueous ink formed on the thin film surface is 80° or more, and contact angle of a droplet of an organic solvent-based ink applied to the thin film composed of a compound containing the group is 40° or more.

The group having lyophilicity provides a thin film composed of a compound containing the group with the lyophilicity. For example, when a droplet of an organic solvent-based ink is formed on a surface of the thin film composed of a compound containing the group having lyophilicity, contact angle of the droplet on the thin film is preferably 5° or less.

As the compound (A), a compound represented by the following formula (1-1) and a compound represented by the following formula (1-2) are suitably used.

[Chem. 9]

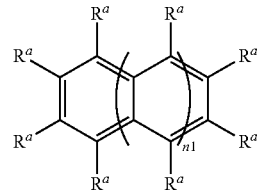

Formula (1-1)

In the formula (1-1), $R^a$s independently represent a hydrogen atom or a substituent. Further, any two adjacent $R^a$s may be coupled with each other to form a ring that is selected from among saturated hydrocarbon rings, unsaturated hydrocarbon rings, aromatic hydrocarbon rings and heterocycles and may have a substituent. At least one of the $R^a$s is a group having lyophilicity. n1 represents an integer of 0 or more.

[Chem. 10]

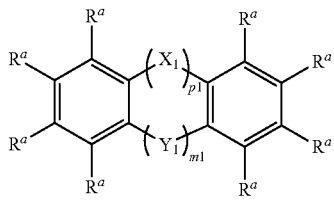

Formula (1-2)

In the formula (1-2), $R^a$s independently represent a hydrogen atom or a substituent. $X_1$ and $Y_1$ may be the same or different and represent —C($R^a$)$_2$—, —N($R^a$)—, —O—, —S—, —Si($R^a$)$_2$—, —B($R^a$)— or —C($R^a$)=C($R^a$)—. Further, any two adjacent $R^a$s may be coupled with each other to form a ring that is selected from among saturated hydrocarbon rings, unsaturated hydrocarbon rings, aromatic hydrocarbon rings and heterocycles and may have a substituent. At least one of the $R^a$s is a group having lyophilicity. p1 and m1 are the same or different and represent an integer of 0 or more.

As $R^a$, an alkyl group, an alkoxy group, an aryl group, an aryloxy group, an arylalkyl group, an arylalkoxy group, an arylalkenyl group, an arylalkynyl group, a monovalent heterocyclic group, an amino group, an acyl group, an acyloxy group, an amide group, a carboxyl group, an alkenyl group, an alkynyl group and an acrylic acid ester group are preferred. n1 is preferably 0 to 4. As $X_1$, —C($R^a$)$_2$— and —N($R^a$)— are preferred. As $Y_1$, —C($R^a$)$_2$— and —N($R^a$)— are preferred. p1 is preferably 0 to 2. m1 is preferably 0 to 2.

Specific examples of the compounds represented by the formulae (1-1) and (1-2) are as follows.

[Chem. 11]

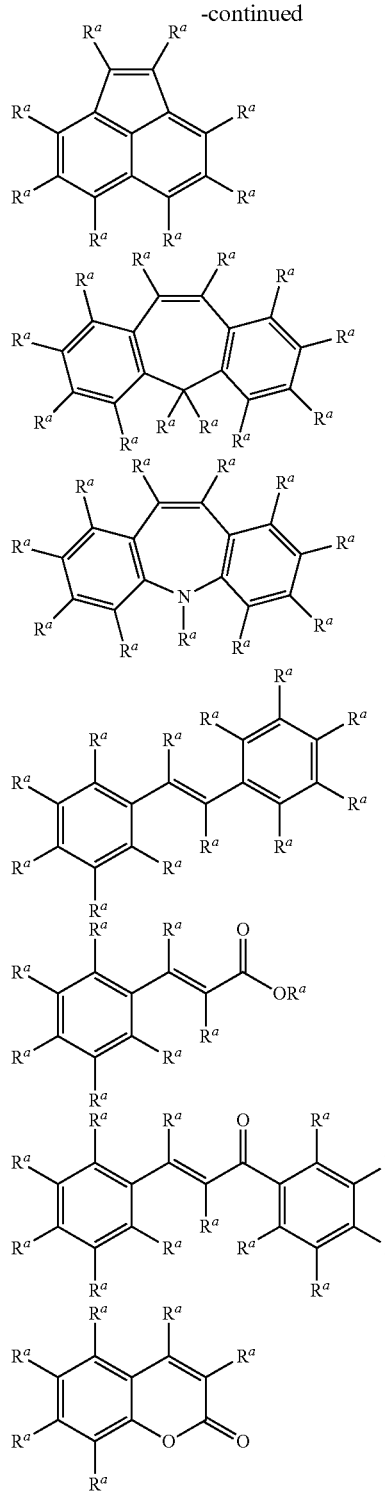

A group represented by $W^2$ is preferably contained in the group having lyophilicity. Examples of $W^2$ include a hydroxyl group, a carboxyl group, an acyl group, an acyloxy group, a halocarbonyl group (it means a group represented by the formula: —C(=O)-E (wherein E represents a halogen atom), and a group represented by the formula: —C(=O)—Cl and a group represented by the formula: —C(=O)—Br are preferred), a halogen atom, an alkoxy group, an aryloxy group, an arylalkoxy group, a phosphoric acid group (a group represented by the formula: (HO)$_2$P(=O)—O—), a group having a phosphate ester structure (a group represented by the formula: (R$^1$O)$_2$P(=O)—O— or the formula: (R$^1$O)(HO)P (=O)—O— (wherein R$^1$ represents an alkyl group, an aryl group, an arylalkyl group, an arylalkenyl group or an arylalkynyl group)), a phosphorous acid group (a group represented by the formula: (HO)$_2$P—O—), a group having a phosphite ester structure (a group represented by the formula: (R$^1$O)$_2$P—O— or the formula: (R$^1$O)(HO)P—O— (wherein R$^1$ is as described above)), a mercapto group, an alkylthio group, an arylthio group, an arylalkylthio group, a heterocyclic thio group, an amino group and the like. Among these, the halogen atom, the alkoxy group, the phosphoric acid group, the amino group and the hydroxyl group are preferred.

The group having lyophilicity is preferably a group containing an atom belonging to Group 4, 5, 6, 13, 14, 15 or 16 of the periodic table. Examples of the atoms belonging to Groups 4, 5, 6, 13, 14, 15 or 16 include atoms belonging to Group 4 such as a titanium atom, a zirconium atom, a hafnium atom and the like; atoms belonging to Group 5 such as a vanadium atom, a niobium atom, a tantalum atom and the like; atoms belonging to Group 6 such as a chromium atom, a molybdenum atom, a tungsten atom and the like; atoms belonging to Group 13 such as a boron atom, an aluminum atom, a gallium atom, an indium atom, a thallium atom and the like; atoms belonging to Group 14 such as a silicon atom, a germanium atom, a tin atom, a lead atom and the like; atoms belonging to Group 15 such as a phosphorus atom, an arsenic atom, an antimony atom, a bismuth atom and the like; atoms belonging to Group 16 such as an oxygen atom, a sulfur atom, a selenium atom, a tellurium, a polonium atom and the like; and the like, but the tin atom, the titanium atom, the zirconium atom, the aluminum atom, the niobium atom, the boron atom, the silicon atom, the phosphorus atom and the sulfur atom are preferred, the zirconium atom, the aluminum atom, the titanium atom, the silicon atom, the phosphorus atom and the sulfur atom are more preferred, the titanium atom and the silicon atom are furthermore preferred, and the silicon atom is particularly preferred.

As the group having lyophilicity, groups including a structure represented by the formula (3) are preferred and groups consisting of a structure represented by the formula (3) are more preferred.

[Chem. 12]

$$—W^1-M^1(W^2)_{v1}(Ra')_{u-v1-1} \quad (3)$$

In the formula (3), M$^1$ represents an atom belonging to Group 4, 5, 6, 13, 14 or 15 of the periodic table. W$^1$ represents a divalent organic group. W$^2$ represents the same meaning as that described above. Ra' represents an alkyl group, an alkoxy group, a hydroxyl group, a halogen atom, an alkenyl group, an alkynyl group, an aryl group, an arylalkyl group, an arylalkenyl group or an arylalkynyl group. v1 is an integer of 1 or more and (u−1) or less. u represents an atomic valence of M$^1$. Where there are a plurality of W$^2$s, these W$^2$s may be the same or different. Where there are a plurality of Ra's, these Ra's may be the same or different.

In the formula (3), Ra' represents an alkyl group, an alkoxy group, a hydroxyl group, a halogen atom, an aryl group, an arylalkyl group, an arylalkenyl group or an arylalkynyl group, and Ra' is preferably an alkyl group, an alkoxy group, a hydroxyl group, a halogen atom, an aryl group or an arylalkyl group. The group represented by Ra' may have a substituent.

In the formula (3), u represents an atomic valence of M$^1$. When M$^1$ is, for example, a silicon atom, a titanium atom, a zirconium atom or the like, u is 4, and when M$^1$ is a boron atom, an aluminum atom or the like, u is 3.

In the formula (3), v1 is an integer of 1 or more and (u−1) or less. v1 is preferably an integer of 2 or more, and more preferably an integer of 3 or more.

Examples of a more preferable embodiment of the group having lyophilicity include a group represented by the following formula.

[Chem. 13]

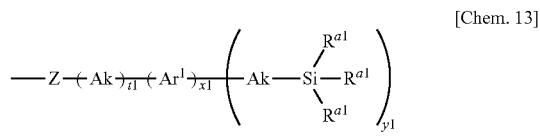

In the formula, Z represents —C(=O)O—, —OC (=O)—, —OC(=O)O—, —C(=O)—, —N(R$^c$)—, —C(=O)N(R$^c$)—, —N(R$^c$)C(=O)—, —N(R$^c$)C(=O)N (R$^c$)—, -Ak-C(=O)O—, -Ak-OC(=O)—, -Ak-OC(=O) O—, -Ak-C(=O)—, -Ak-N(R$^c$)—, -Ak-C(=O) N(R$^c$)—, -Ak-N(R$^c$)C(=O)—, -Ak-N(R$^c$)C(=O)N(R$^c$)—, —O—, —S— or -Ak-, Ar$^1$ represents an aromatic hydrocarbon group having a valence of (1+y1) or a heterocyclic group having a valence of (1+y1), Ak represents an alkylene group having 1 to 12 carbon atoms, R$^{a1}$ represents a hydrogen atom, a halogen atom, a hydroxyl group, an alkoxy group or an alkyl group, and R$^c$ represents a hydrogen atom or a substituent. Where there are a plurality of R$^c$s, these R$^c$s may be the same or different. t1 represents 0 or 1, x1 represents 0 or 1, and y1 represents an integer of 1 or more. A plurality of R$^{a1}$s may be the same or different. Where there are a plurality of Aks, these Aks may be the same or different.

As R$^{a1}$, a hydroxyl group, an alkoxy group and a halogen atom are preferred. As Ak, alkylene groups having 1 to 6 carbon atoms are preferred. Further, as Z, —C(=O)O—, —OC(=O)—, —C(=O)—, —N(R$^c$)—, —C(=O)N (R$^c$)—, —N(R$^c$)C(=O)—, —O— and -Ak- are preferred. x1 is preferably 1, and y1 is preferably 1 to 3.

Specific examples of the compound containing a group having liquid-repellency are as follows.

[Chem. 14]

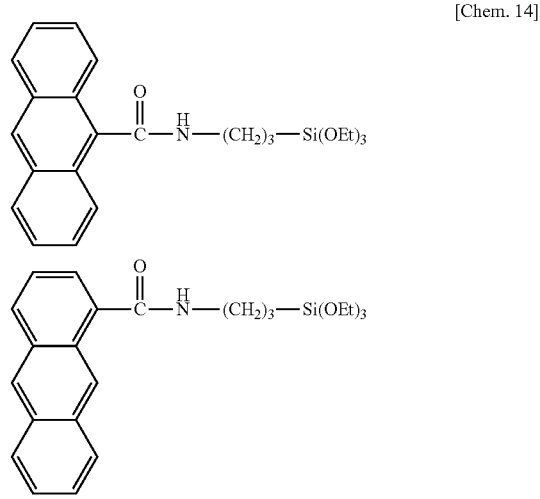

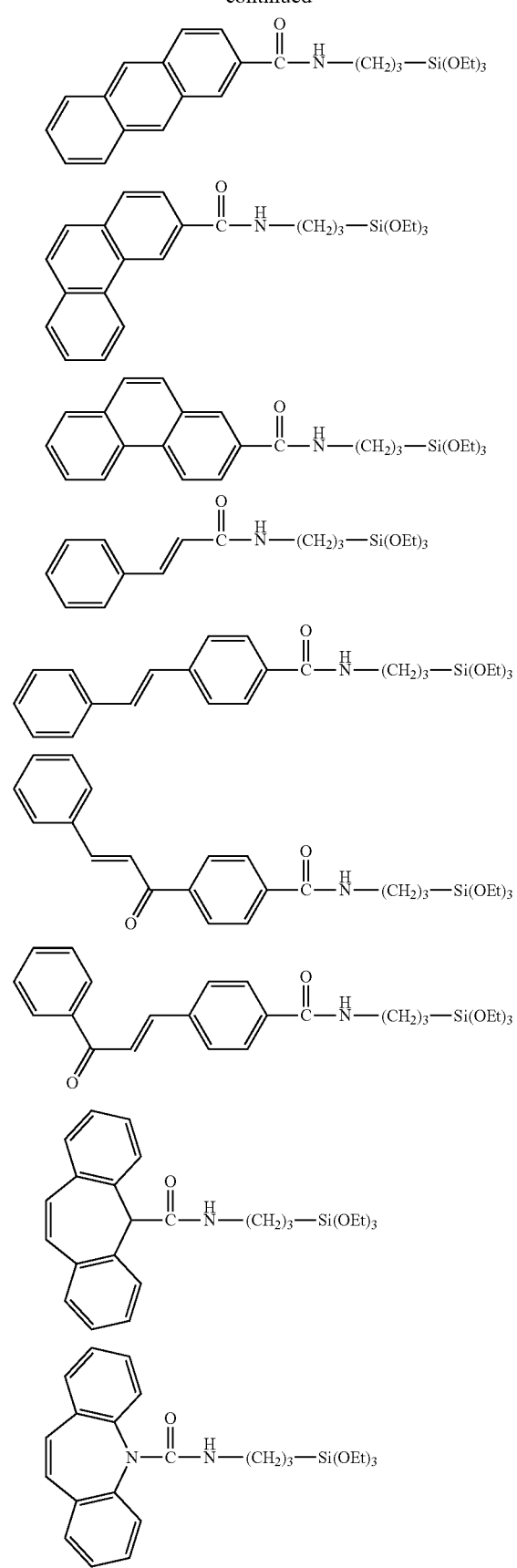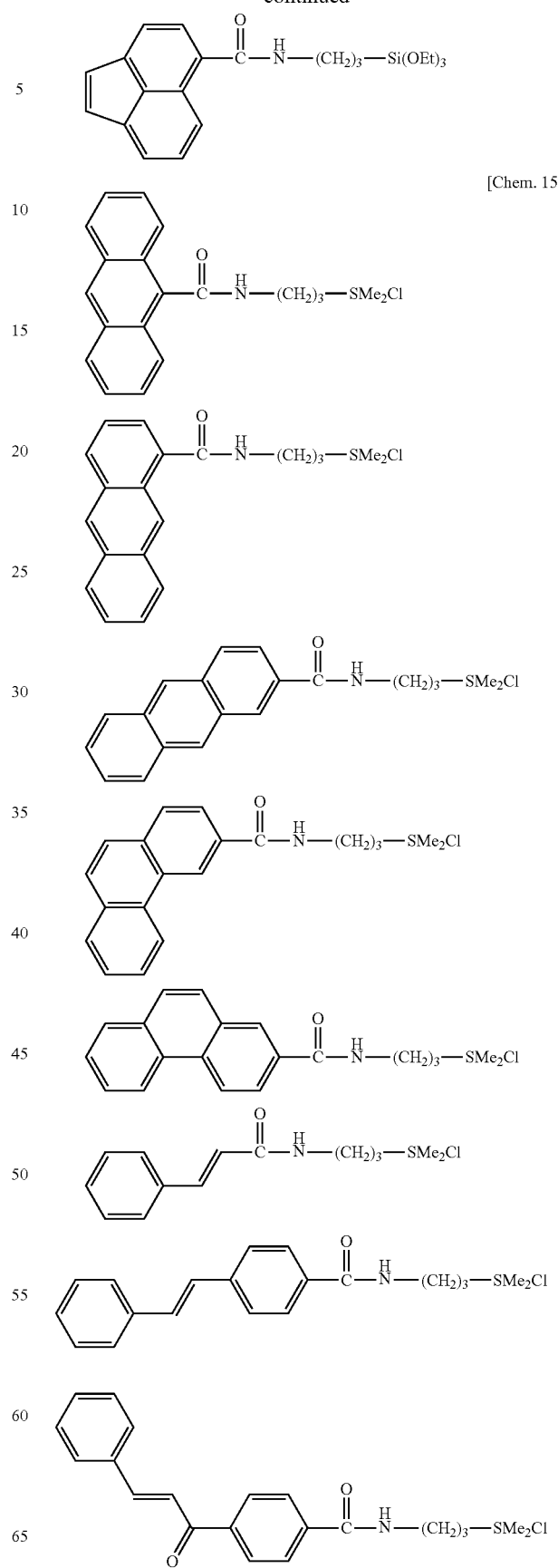

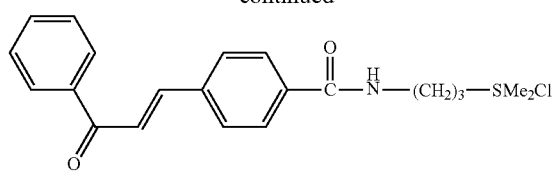
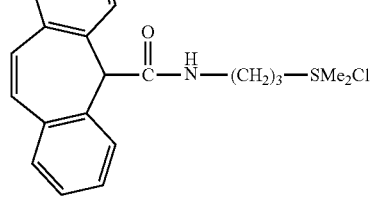
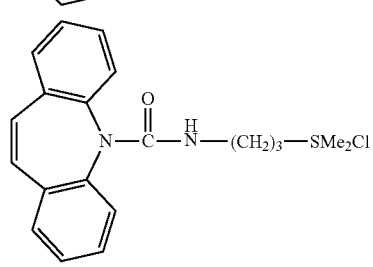
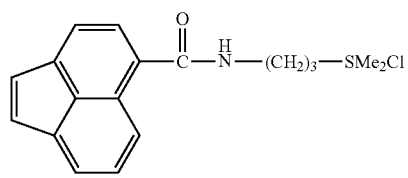
[Chem. 16]
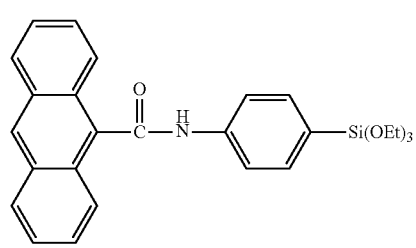
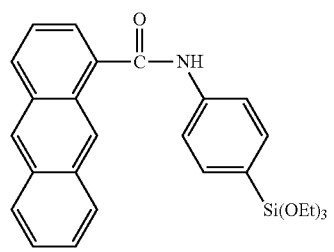
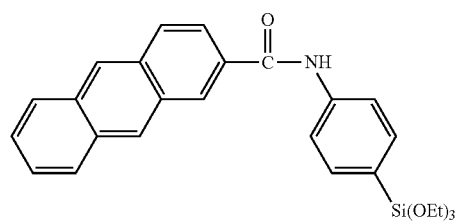
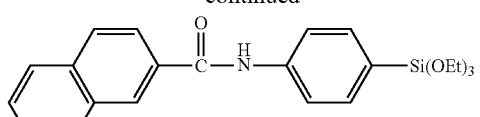
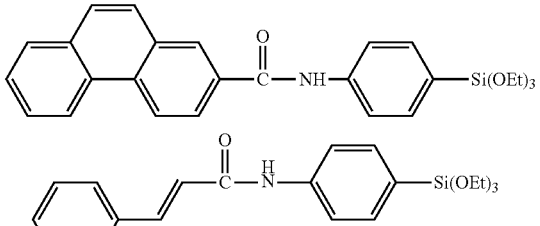
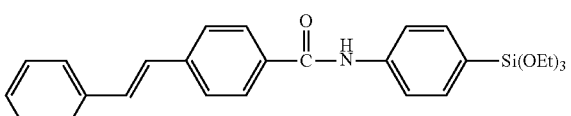
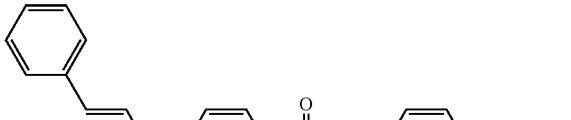
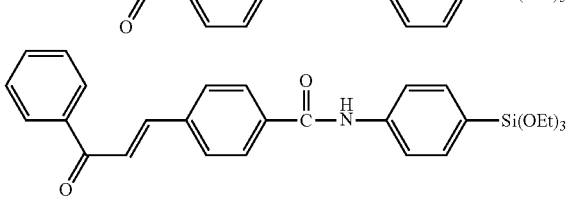
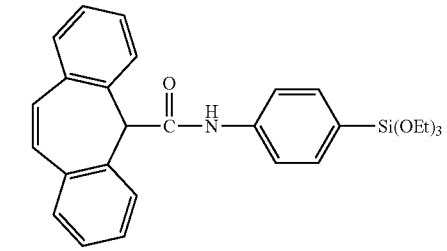
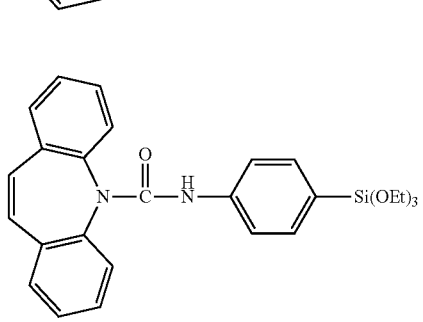
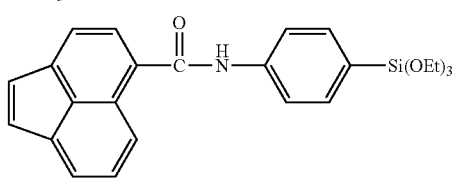

-continued

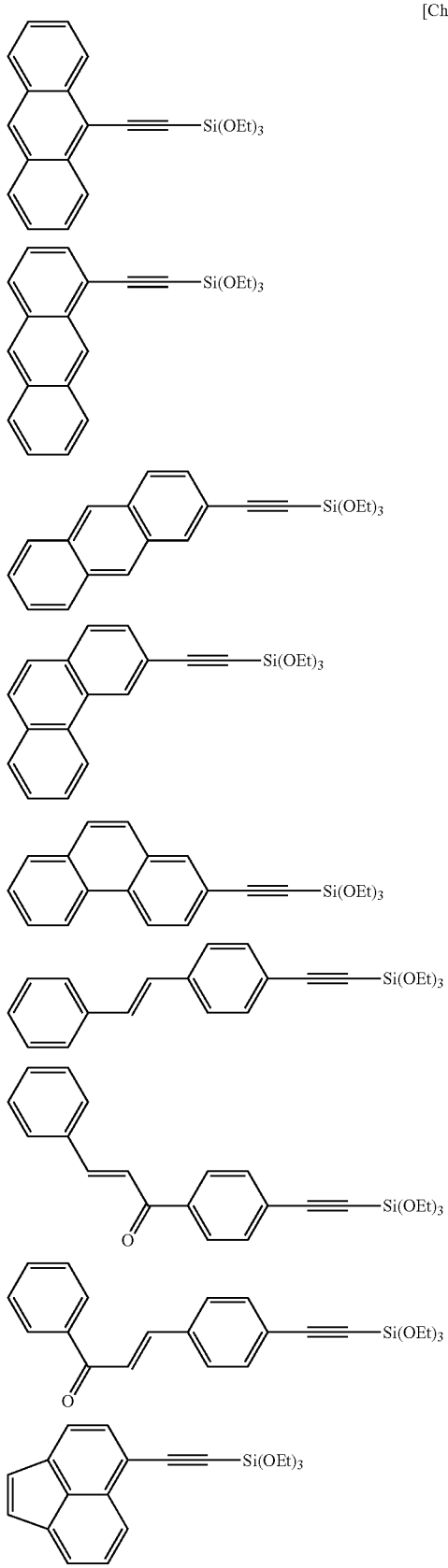

As the compound (B), a compound represented by the formula (2-1) and a compound represented by the formula (2-2) are suitably used.

[Chem. 18]

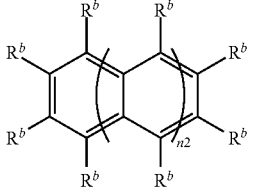

Formula (2-1)

In the formula (2-1), $R^b$s independently represent a hydrogen atom or a substituent. Further, any two adjacent $R^b$s may be coupled with each other to form a ring that is selected from among saturated hydrocarbon rings, unsaturated hydrocarbon rings, aromatic hydrocarbon rings and heterocycles and may have a substituent. At least one of the $R^b$s is a group having liquid-repellency. n2 represents an integer of 0 or more.

Further, groups having a partial structure (2-2) represented by the following formula are also suitably used.

[Chem. 19]

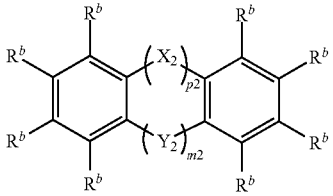

Formula (2-2)

In the formula (2-2), $R^b$s independently represent a hydrogen atom or a substituent. $X_2$ and $Y_2$ may be the same or different and represent $-C(R^b)_2-$, $-N(R^b)-$, $-O-$, $-S-$, $-Si(R^b)_2-$, $-B(R^b)-$ or $-C(R^b)=C(R^b)-$. Further, any two adjacent $R^b$s may be coupled with each other to form a ring that is selected from among saturated hydrocarbon rings, unsaturated hydrocarbon rings, aromatic hydrocarbon rings and heterocycles and may have a substituent. At least one of the $R^b$s is a group having liquid-repellency. p2 and m2 are the same or different and represent an integer of 0 or more.

As $R^b$, an alkyl group, an alkoxy group, an aryl group, an aryloxy group, an arylalkyl group, an arylalkoxy group, an arylalkenyl group, an arylalkynyl group, a monovalent heterocyclic group, an amino group, an acyl group, an acyloxy group, an amide group, a carboxyl group, an alkenyl group, an alkynyl group and an acrylic acid ester group are preferred. n2 is preferably 0 to 4. As $X_2$, $-C(R^b)_2-$ and $-N(R^b)-$ are preferred. As $Y_2$, $-C(R^b)_2-$ and $-N(R^b)-$ are preferred. p2 is preferably 0 to 2. m2 is preferably 0 to 2.

Specific examples of the compounds represented by the formulae (2-1) and (2-2) are as follows.

[Chem. 20]

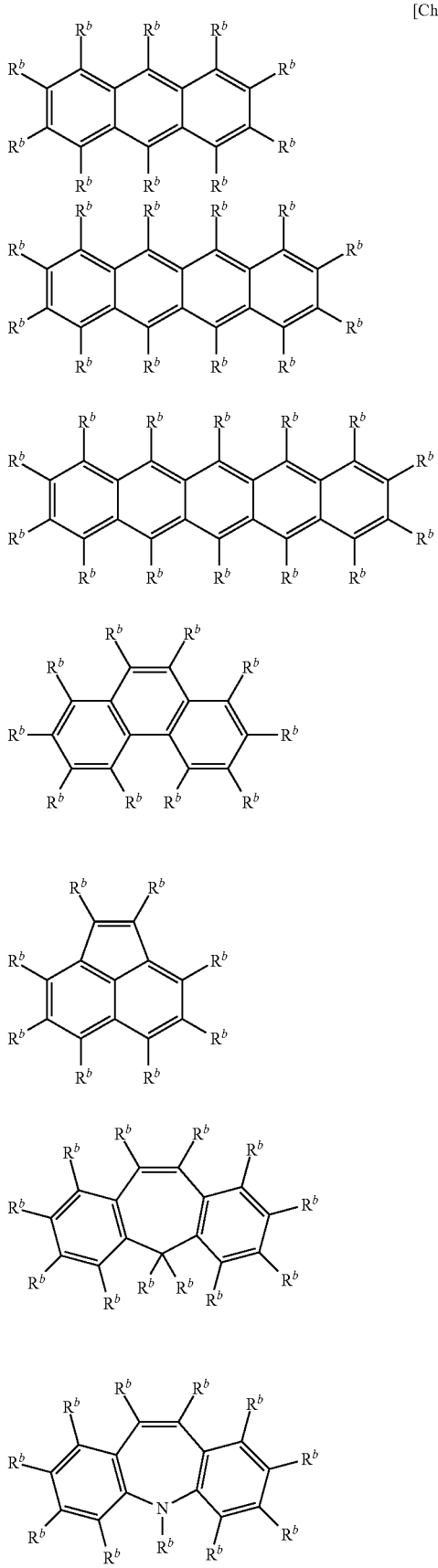

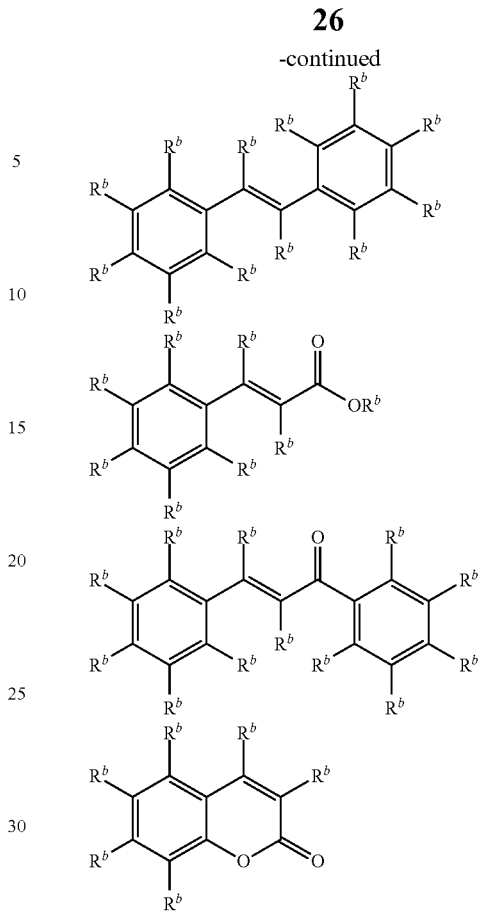

Examples of the group having liquid-repellency include groups including the following structure containing a fluorine atom.

[Chem. 21]

$$—(B)_{n3}—R^{b1} \qquad (4)$$

In the formula (4), B represents a divalent group composed of atoms other than fluorine. Further, $R^{b1}$ represents a monovalent organic group containing a fluorine atom. n3 represents an integer of 0 to 3, and where there are a plurality of Bs, these Bs may be the same or different. B is preferably —O—, an aromatic hydrocarbon group, a heterocyclic group, an alkyl group or an alkyloxy group.

Examples of a preferable embodiment of the group having liquid-repellency include a group represented by the following formula.

[Chem. 22]

$$—Z—(Ak)_{\overline{t2}}(Ar^2)_{\overline{x2}}(R^{b1})_{y2}$$

In the formula, Z represents —C(=O)O—, —OC(=O)—, —OC(=O)O—, —C(=O)—, —N($R^c$)—, —C(=O)N($R^c$)—, —N($R^c$)C(=O)—, —N($R^c$)C(=O)N($R^c$)—, -Ak-C(=O)O—, -Ak-OC(=O)—, -Ak-OC(=O)O—, -Ak-C(=O)—, -Ak-N($R^c$)—, -Ak-C(=O)N($R^c$)—, -Ak-N($R^c$)C(=O)—, -Ak-N($R^c$)C(=O)N($R^c$)—, —O—, —S— or -Ak-, Ak represents an alkylene group having 1 to 12 carbon atoms, and $R^c$ represents a hydrogen atom or a substituent. Where there are a plurality of $R^c$s, these $R^c$s may be the same or different. $Ar^2$ represents an aromatic hydrocarbon group having a valence of (1+y2) or a heterocyclic group having a valence of (1+y2), $R^{b1}$ represents a monovalent organic group containing a fluorine atom, t2 represents 0 or 1, x2 represents 0 or 1, and y2 represents an integer of 1 or more. Where there are a plurality of $R^{b1}$s, these $R^{b1}$s may be the same or different.

Examples of a preferable embodiment of the group having liquid-repellency include a group represented by the following formula.

[Chem. 23]

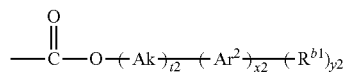

In the formula, $Ar^2$, $R^{b1}$, Ak, t2, x2 and y2 respectively represent the same meanings as those described above.

$R^{b1}$, a monovalent organic group containing a fluorine atom, is a group in which a fluorine atom is substituted for one or more hydrogen atoms in the organic group. Particularly, the organic group is preferably an alkyl group, an aryl group, an arylalkyl group, an arylalkenyl group or an arylalkynyl group, and more preferably an alkyl group. The number of carbon atoms of the alkyl group is preferably from 1 to 20, more preferably from 4 to 18, and moreover preferably from 6 to 17 from the viewpoint of liquid-repellency.

With respect to the number of fluorine atoms in $R^{b1}$, a value obtained by dividing the number of fluorine atoms in $R^{b1}$ by the sum of the number of fluorine atoms in $R^{b1}$ and the number of hydrogen atoms in $R^{b1}$ (substitutional rate) is preferably 50% or more, and more preferably 70% or more from the viewpoint of liquid-repellency. Particularly, when the organic group is an alkyl group, a so-called perfluoroalkyl group, in which fluorine atoms are substituted for all hydrogen atoms of the organic group, is preferred from the viewpoint of liquid-repellency.

As $Ar^2$, a phenylene group, a phenyltriyl group, a phenyltetrayl group, a naphthalenediyl group, a naphthalenetriyl group, a naphthalenetetrayl group, an anthracenediyl group, an anthracenetetrayl group, a fluorenediyl group and a fluorenetriyl group are preferred. t2 is preferably 1. x2 is preferably 1. y2 is preferably from 1 to 5.

Examples of a more preferable embodiment of the group having liquid-repellency include a group represented by the following formula.

[Chem. 24]

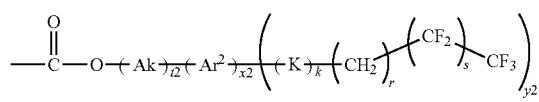

In the formula, $Ar^2$, Ak, t2, x2 and y2 respectively represent the same meanings as those described above. K represents —O—, —S—, —NH— or —NR—. R represents an alkyl group or an aryl group. k represents 0 or 1, r represents an integer of 0 to 6, and s represents an integer of 0 to 16. Where there are a plurality of k's, these k's may be the same or different. Where there are a plurality of r's, these r's may be the same or different. Where there are a plurality of s's, these s's may be the same or different.

As K, —O—, —S— and —NR— are preferred. k is preferably 1. r is preferably from 0 to 3. s is preferably from 1 to 10.

Specific examples of the compound containing a group having liquid-repellency are as follows.

[Chem. 25]

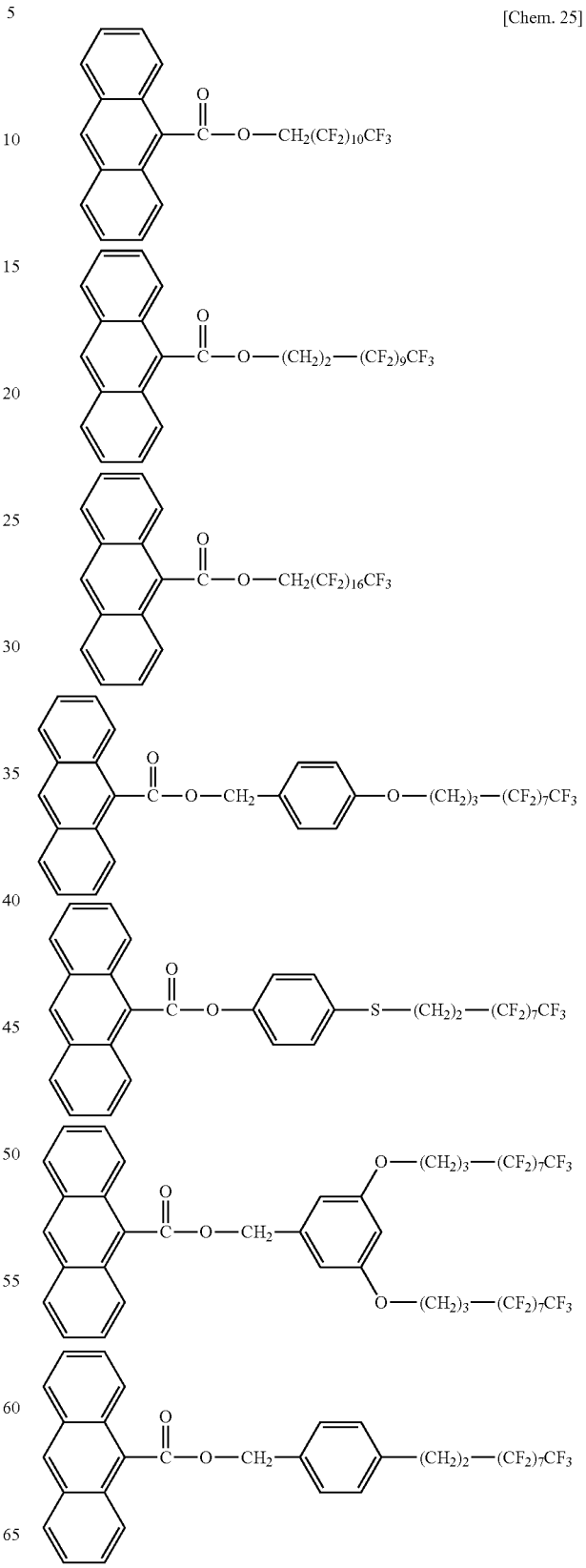

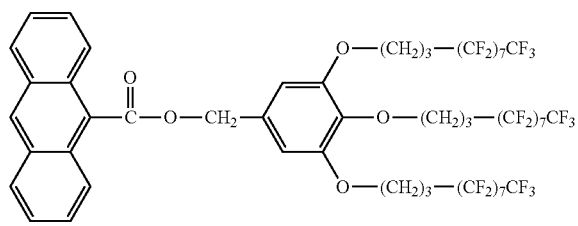
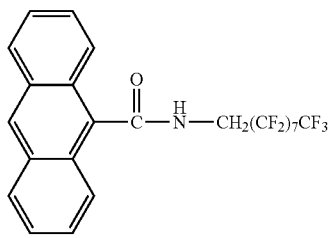
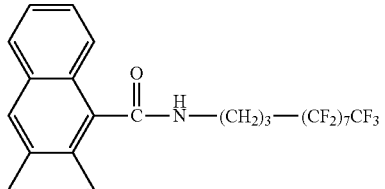
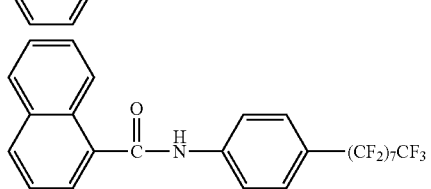
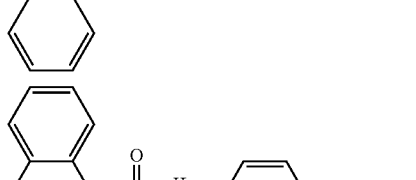
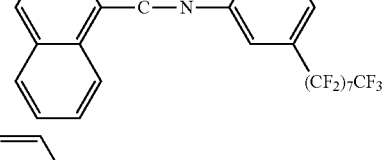
[Chem. 26]
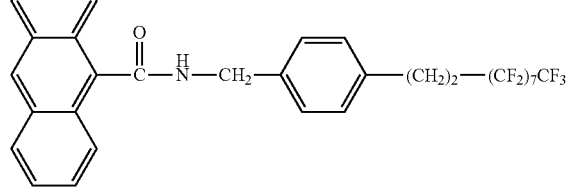
[Chem. 27]
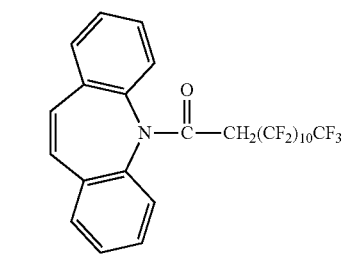
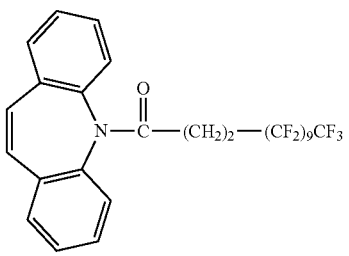
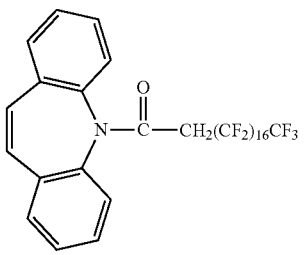
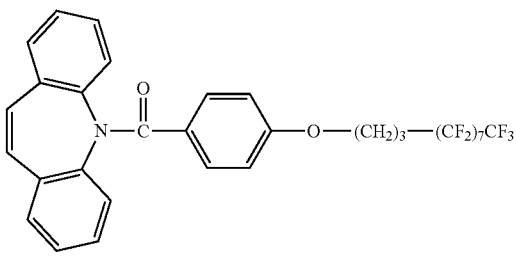
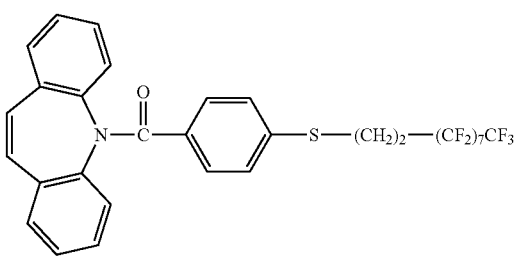
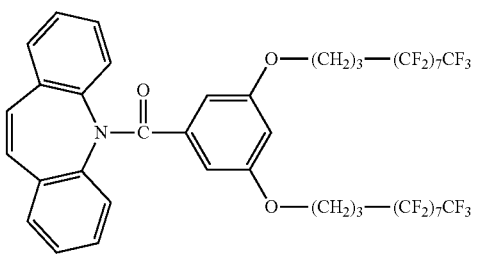
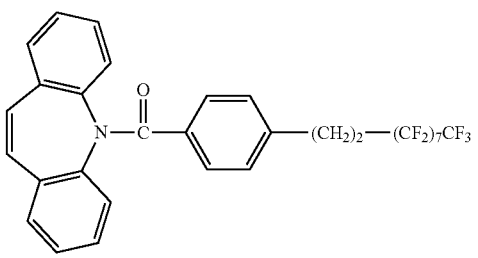

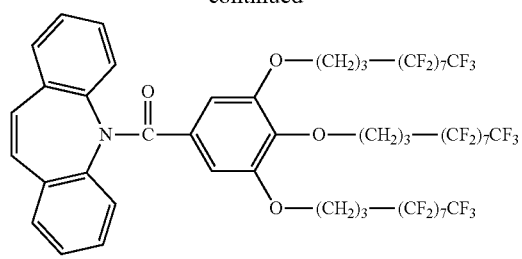
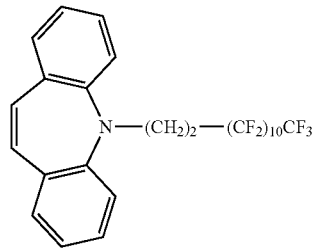
[Chem. 28]
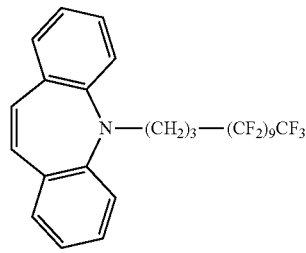
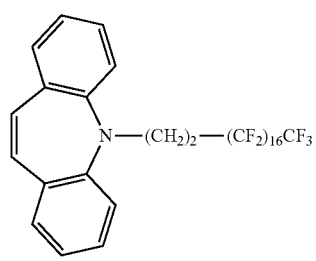
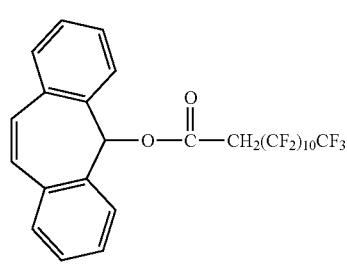
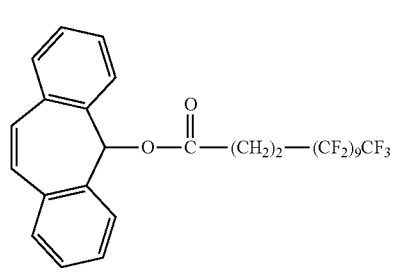
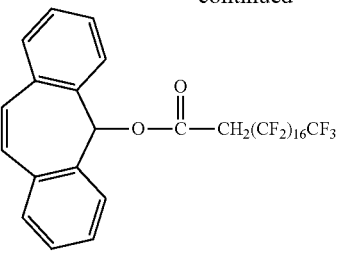
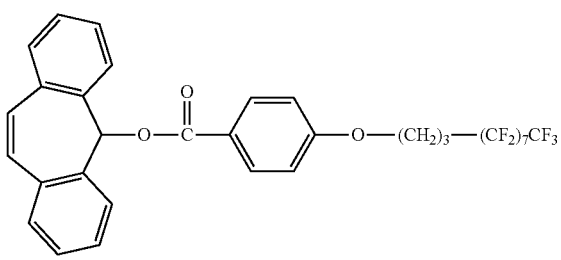
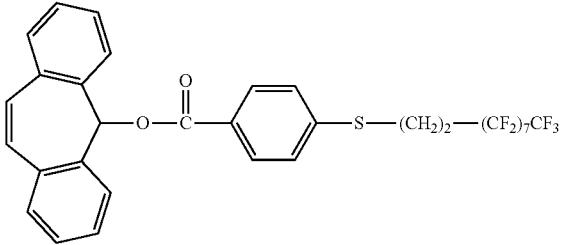
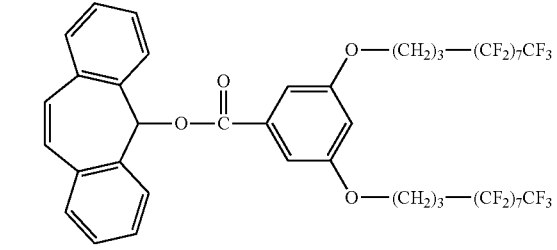
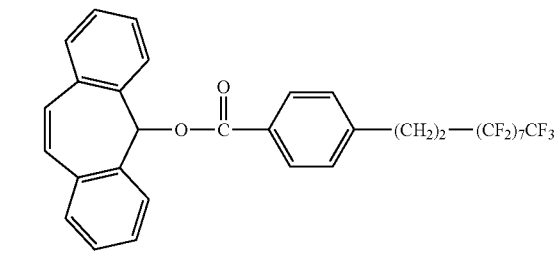
[Chem. 29]
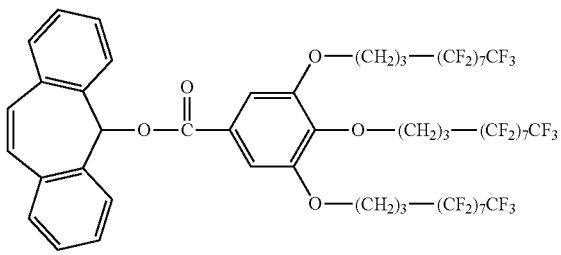
In the present invention, the method of dimerizing the compound (A) and the compound (B) is carried out by light irradiation. Light used in the light irradiation is not particularly limited as long as it is light in a range of wavelengths where this compound absorbs its light energy and initiate a dimerization reaction. For example, light having a wavelength of 200 nm or more and 380 nm or less is preferred. Since light having a wavelength less than 200 nm has very intense energy, there is a possibility of causing decomposition of a base material or a compound. Further, light having a wavelength more than 380 nm is likely in large possibility to become the light which this compound hardly absorbs. The irradiation time is appropriately changed in accordance with wavelength of light, intensity of light, type of a light source, type of the compound and the like.

Examples of the light source include a low-pressure mercury lamp, a high-pressure mercury lamp, an ultra high-pressure mercury lamp, a xenone lamp, a sodium lamp, a gas laser using nitrogen or the like, a liquid laser of an organic dye solution, a solid laser using an inorganic single crystal containing rare-earth ions, and the like. Further, as a light source giving monochromatic light other than a laser, light with a specific wavelength, in which a broadband line spectrum or a continuous spectrum is extracted by use of an optical filter such as a band-pass filter or a cut-off filter, may be employed. As the light source, a high-pressure mercury lamp or an ultra high-pressure mercury lamp is preferred because a large area can be irradiated at once.

In the present invention, as an embodiment of a compound to be formed by the method of dimerizing the compound (A) and the compound (B) by light irradiation, there is a compound which is bound by a saturated cyclic structure or an unsaturated cyclic structure. As the compound which is bound by a saturated cyclic structure or an unsaturated cyclic structure, there is a compound bound with a cycloalkane structure, a cycloalkene structure or a cycloalkadiene structure.

Specific examples of the present invention include the following compounds and the like.

[Chem. 30]

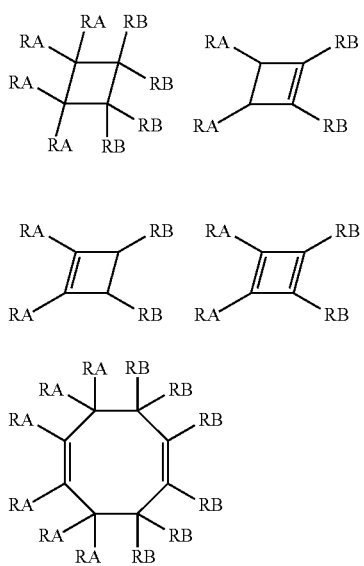

In the formulae, RA is a group derived from the compound (A) and RB is a group derived from the compound (B).

[Chem. 31]

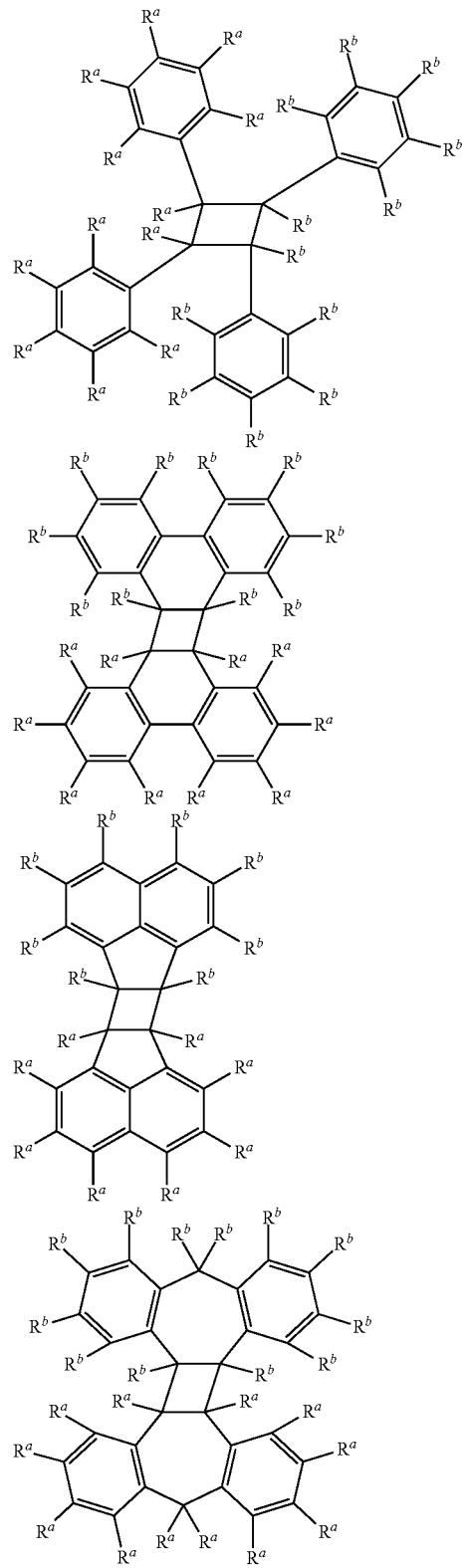

In the formulae, $R^a$ and $R^b$ respectively represent the same meanings as those described above.

[Chem. 32]

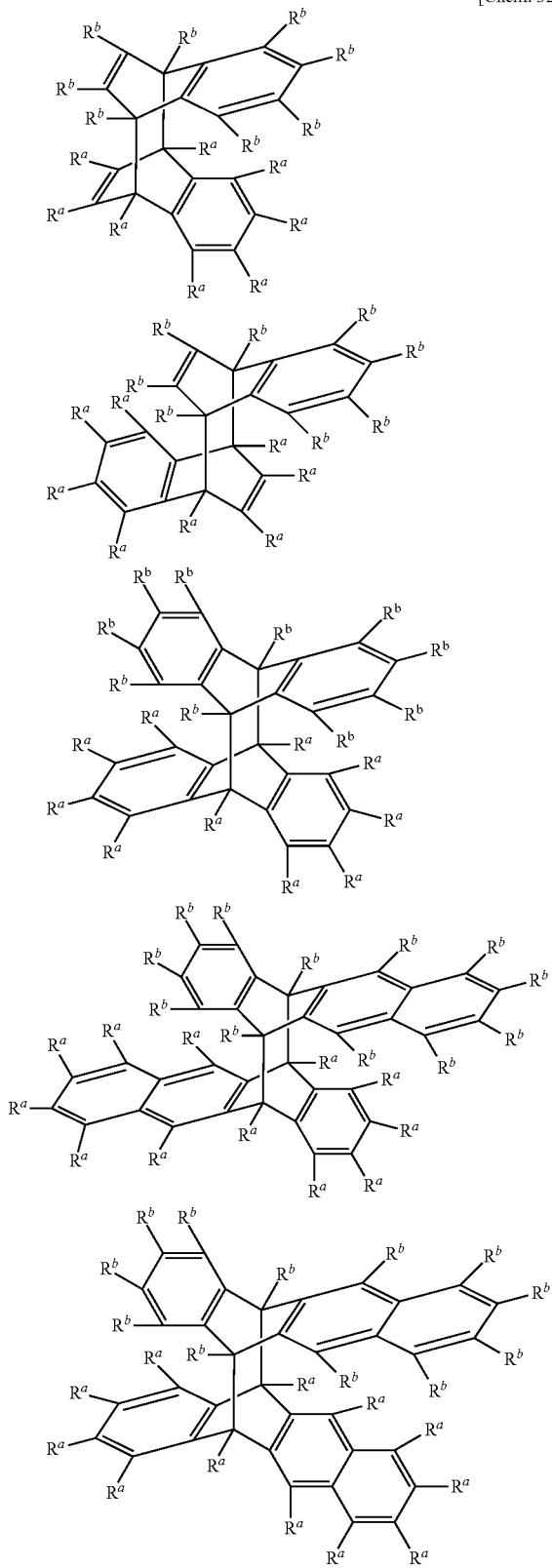

In the formulae, $R^a$ and $R^b$ respectively represent the same meanings as those described above.

It will be described below a method for using a compound of the present invention in order to perform the patterning of a lyophilic region and a liquid-repellent region by irradiation of light.

First, a substrate such as glass, a substrate with ITO (indium tin oxide) or a silicon wafer is cleaned by using a usual wet cleaning method/dry cleaning method. Then, a solution obtained by dissolving the compound (A) in an organic solvent is applied onto the substrate. A solvent to be used is not particularly limited as long as the compound (A) is soluble therein, but alcohols such as methanol, ethanol, isopropanol and the like; esters such as ethyl acetate, butyl acetate and the like; hydrocarbons such as hexane and the like; and aromatics such as toluene, xylene and the like are preferred. Concentration of the compound (A) in the solution is preferably 0.01 to 50% by weight, and more preferably 0.1 to 10% by weight.

A method of applying the solution is not particularly limited, and coating methods such as spin coating, dip coating, wire bar coating, blade coating, roll coating and the like, printing methods such as ink-jetting, flexo printing and the like, and the like can be employed. Application is preferably performed at room temperature. Next, a base material in which a film has been formed on a substrate is heated and dried in the air or in a nitrogen stream. When a surface of the base material has a hydroxyl group, and the compound (A) contains a group having titanium or silicon and contains a group serving as a so-called titanium coupling agent or silane coupling agent, the group reacts with a hydroxyl group on the substrate through the above-mentioned heating and drying to fix the compound (A) onto the substrate.

After heating and drying the substrate, a solution obtained by dissolving the compound (B) in an organic solvent is applied onto the surface on which a film is formed by applying the compound (A). A solvent to be used is not particularly limited as long as the compound (B) is soluble therein, but alcohols such as methanol, ethanol, isopropanol and the like; esters such as ethyl acetate, butyl acetate and the like; hydrocarbons such as hexane and the like; and aromatics such as toluene, xylene and the like are preferred, and among these, a solvent containing a fluorine atom is more preferred. Concentration of the compound (B) in the solution is preferably 0.01 to 50% by weight, and more preferably 0.1 to 10% by weight.

After applying the compound (B), the base material is heated and dried in a nitrogen stream, and then irradiated with light. Light used in light irradiation is as described above. Light irradiation is preferably carried out through a photomask. By this method, it is possible to initiate a photodimerization reaction only in a desired region at the surface of a film and to obtain a treated base material in which the lyophilic region and the liquid-repellent region form a desired pattern. An atmosphere of light irradiation can be selected arbitrarily, but it is more preferred to perform light irradiation in an atmosphere of an inert gas such as a nitrogen gas. The inert gases include a gas selected from nitrogen, argon, helium, carbon dioxide and the like, and a nitrogen gas is most preferable because it is available at low cost.

After the light irradiation, the unreacted compound (B) present at the surface of the base material is removed. As a method of removing the unreacted compound (B), a method of washing the substrate with a solvent in which the unreacted compound (B) is soluble is preferred. The solvent used in washing is not particularly limited as long as it is a solvent in which the compound (B) is soluble but the compound (A) is insoluble, and a solvent containing a fluorine atom is preferred.

Since the compound obtained by dimerizing the compound (A) and the compound (B) is present in the region thus irradiated with light, the region exhibits liquid-repellency by the effect of a liquid-repellent group of the compound (B). On the other hand, the region which is not irradiated with light does not exhibit liquid-repellency and becomes relatively lyophilic since the compound (B) is removed by washing and therefore the compound (A) is bonded to the substrate.

By using a compound of the present invention, a lyophilic region and a liquid-repellent region can be patterned by light irradiation without using a large-scale apparatus and a light source. For example, when a functional material is applied to the patterned surface by a slot coating method, a spraying method or the like, the solution is not applied to the liquid-repellent region and is held only in the lyophilic region, and therefore a thin film in which the functional material is elaborately patterned is obtained after drying. The patterned functional thin film thus obtained can be usefully used in the field of an organic thin film transistor device, an organic thin film solar cell, an organic EL display and the like.

EXAMPLES

Hereinafter, the present invention will be described specifically with reference to the examples, but the present invention is not limited to these examples.

Synthesis Example 1

Synthesis of Compound 1

[Chem. 33]

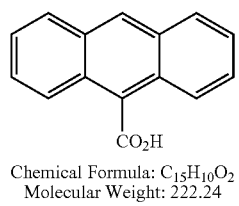

Chemical Formula: $C_{15}H_{10}O_2$
Molecular Weight: 222.24

APS, DCC, HOBt, Et$_3$N
dry CH$_2$Cl$_2$

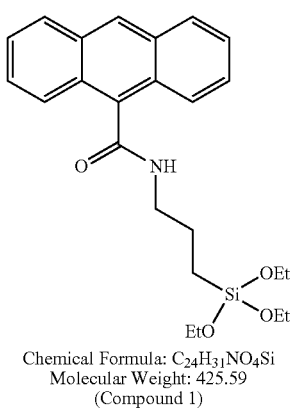

Chemical Formula: $C_{24}H_{31}NO_4Si$
Molecular Weight: 425.59
(Compound 1)

Into a 200 ml two-necked eggplant flask, 1.0 g (4.5 mmol) of 9-anthracenecarboxilic acid, 0.93 g (4.5 mmol) of DCC(N,N'-dicyclohexylcarbodiimide) and 0.61 g (4.5 mmol) of HOBt (1-hydroxybenzotriazole) were put, and the flask was deaerated and the atmosphere in the flask was replaced with argon. To this, 360 ml of dry CH$_2$Cl$_2$ (dehydrated methylene chloride), 1.0 g (4.5 mmol) of APS (3-aminopropyltrimethoxysilane) and 0.45 g (4.5 mmol) of Et$_3$N (triethylamine) were added, and the resulting mixture was magnetically stirred at room temperature for 24 hours. Since the progress of a reaction was confirmed by use of TLC (developing solvent: chloroform), the reaction was terminated, and after the solvent was distilled off under a reduced pressure, the product was purified by column chromatography (silica gel, developing solvent: chloroform). The yield was 360 mg (0.85 mmol, percent yield 20%).

$^1$H NMR (CDCl$_3$): δ=8.46 (s, 1H), 8.07 (d, 2H), 7.99 (d, 2H), 7.48 (m, 4H), 6.42 (s, 1H), 3.75 (m, 6H), 1.90 (m, 2H), 1.25 (m, 2H), 1.12 (m, 9H), 0.77 (t, 2H)

Synthesis Example 2

Synthesis of Compound 2-1

[Chem. 34]

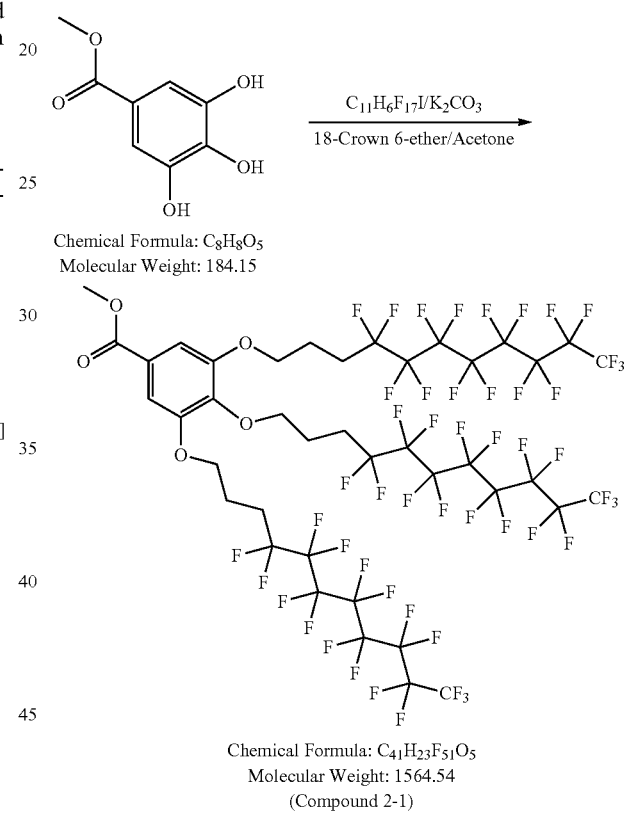

Chemical Formula: $C_8H_8O_5$
Molecular Weight: 184.15

$C_{11}H_6F_{17}I/K_2CO_3$
18-Crown 6-ether/Acetone

Chemical Formula: $C_{41}H_{23}F_{51}O_5$
Molecular Weight: 1564.54
(Compound 2-1)

Into a three-necked round-bottom flask equipped with a Dimroth condenser and a septum cover, 268 mg (1.5 mmol, 1.0 eq.) of methyl gallate, 3.0 g (0.51 mmol, 3.5 eq.) of heptadecafluoroundecyliodo, 115 mg (0.043 mmol, 0.3 eq.) of 18-crown 6-ether, and 760 mg of potassium carbonate were put, and the flask was deaerated and the atmosphere in the flask was replaced with argon. 20 ml of dehydrated acetone was added and the resulting mixture was refluxed for 3 days. After confirming that the raw material was dissipated by use of TLC (developing solvent: hexane/ethyl acetate=5/1), the reactant was washed with distilled water and dried over anhydrous sodium sulfate, and then the solvent was distilled off under a reduced pressure. Purification of the product was carried out through recrystallization (acetone). The yield of a compound 2-1 was 2.0 g (1.3 mmol, percent yield 89%).

$^1$H NMR (CDCl$_3$): δ=7.28 (s, 2H), 4.11 (t, 3H), 4.05 (t, 2H), 3.89 (s, 3H), 2.33 (m, 6H), 2.15 (m, 4H), 2.08 (m, 2H)

Synthesis Example 3
Synthesis of Compound 2-2
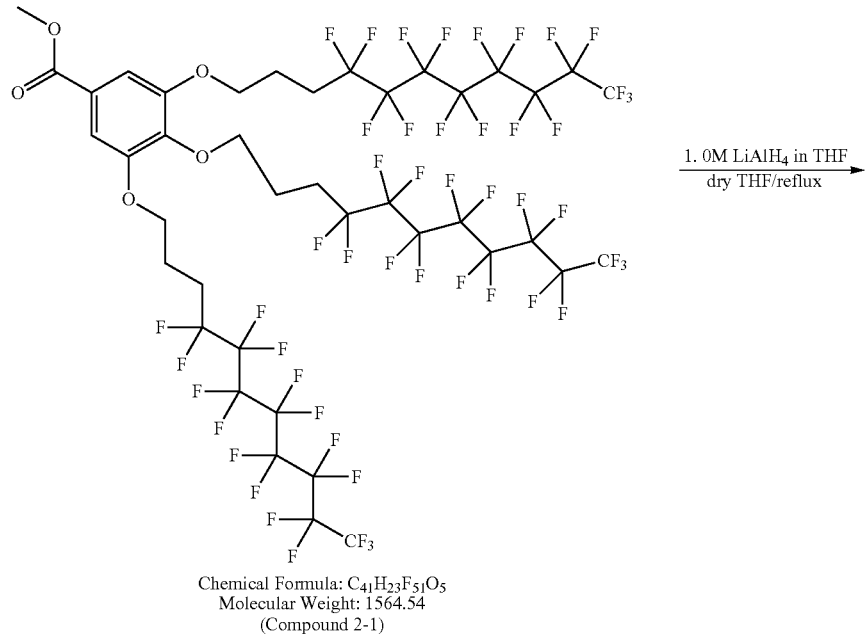
Chemical Formula: C₄₁H₂₃F₅₁O₅
Molecular Weight: 1564.54
(Compound 2-1)
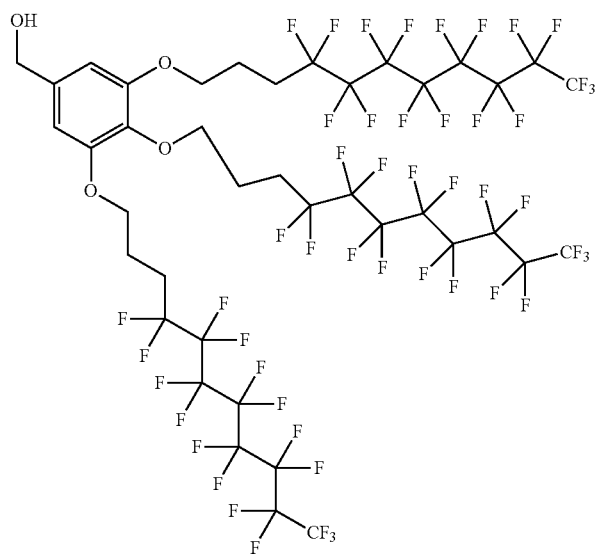
Chemical Formula: C₄₀H₂₃F₅₁O₄
Molecular Weight: 1536.53
(Compound 2-2)

Into a 100 ml three-necked round-bottom flask equipped with a Dimroth condenser and a septum cover, 49.5 mg (1.9 mmol, 2.0 eq.) of lithium aluminum hydride was put, and the flask was deaerated and the atmosphere in the flask was replaced with argon. To this, 10 ml of dehydrated THF (tetrahydrofuran) and 1.5 g (1.0 mmol) of the compound 2-1 were added and the resulting mixture was refluxed for 2 hours. After confirming that the raw material was dissipated by use of TLC (developing solvent: hexane/ethyl acetate=1/1), the solvent was distilled off under a reduced pressure. Purification of the product was carried out through recrystallization (acetone). The yield of a compound 2-2 was 1.4 g (0.91 mmol, percent yield 91%).

$^1$H NMR (CDCl$_3$): δ=6.59 (s, 2H), 4.60 (d, 2H), 4.06 (t, 4H), 3.97 (t, 2H), 2.33 (m, 6H), 2.15 (m, 4H), 2.08 (m, 2H)

Synthesis Example 4

Synthesis of Compound 2

[Chem. 36]

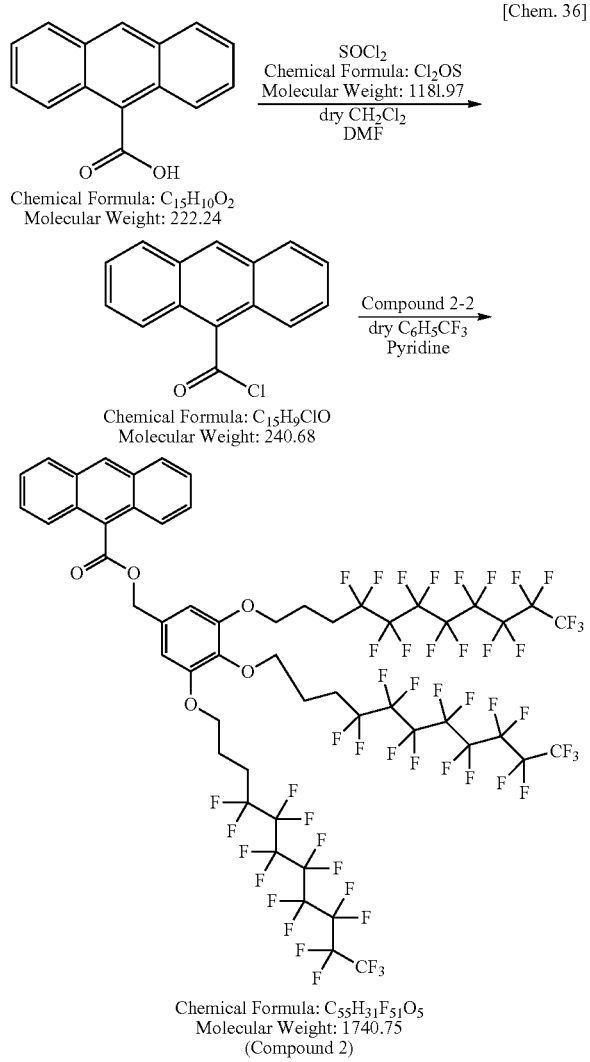

Into a 100 ml two-necked eggplant flask equipped with a Dimroth condenser, 17.3 mg (0.078 mmol) of 9-anthracenecarboxilic acid was put, and the flask was deaerated and the atmosphere in the flask was replaced with argon. To this, 5 ml of dry CH$_2$Cl$_2$ (dehydrated dichloromethane), 50 ml of DMF (N,N-dimethylformamide) and 13 mg (16.7 mmol) of thionylchloride were added, and the resulting mixture was refluxed for 0.5 hour at room temperature and then for 4 hours. After stirring the solution, the solvent was distilled off under a reduced pressure, and 100 mg (0.065 mmol) of the compound 2-2, 10 ml of dehydrated trifluorotoluene and 0.5 ml of pyridine were added and the resulting mixture was magnetically stirred at room temperature for 24 hours. After the reaction, the reactant was washed with distilled water, dried over anhydrous sodium sulfate, and then purified through recrystallization (acetone). The yield of a compound 2 was 31 mg (0.018 mmol, percent yield 27%).

Example 1

Next, examples will be described. First, a glass substrate was cleaned by the following procedure. That is, the substrate was subjected to ultrasonic cleaning using acetone for 30 minutes and then subjected to UV ozone cleaning for 15 minutes.

Next, the compound 1 prepared above was dissolved in a mixed solvent of equal parts of dehydrated dichloroethylene and dehydrated toluene at a concentration of 4 mM with respect to the solvent to form a solution of the compound 1. The glass substrate subjected to ultrasonic cleaning was immersed in the solution of the compound 1 for 20 minutes.

Thereafter, the glass substrate was taken out and dried at 110° C. for 20 minutes in the air with a hot plate. After drying, chloroform was poured over the glass substrate to remove the excess compound 1 and form a film containing the compound 1.

Next, the compound 2 prepared above was dissolved in chloroform at a concentration of 1 mM with respect to chloroform to form a solution of the compound 2. The substrate having the applied compound 1 was immersed in the solution of the compound 2 for 20 minutes. Thereafter, the glass substrate was taken out and naturally dried in the air to form a film containing the compound 2 on the film containing the compound 1.

Next, the film containing the compound 2 was irradiated with ultraviolet light. The ultraviolet irradiation was performed at the intensity of 51 mW/cm$^2$ for 20 minutes by use of light with a wavelength of 365 nm with a conventional light source. After irradiation, trifluorotoluene was poured over the whole substrate to remove the unreacted compound 2. The compound 1 and the compound 2 were photodimerized in the part irradiated with light to produce the following compound. The following compound contains a group having liquid-repellency, and forms a liquid-repellent region.

[Chem. 37]

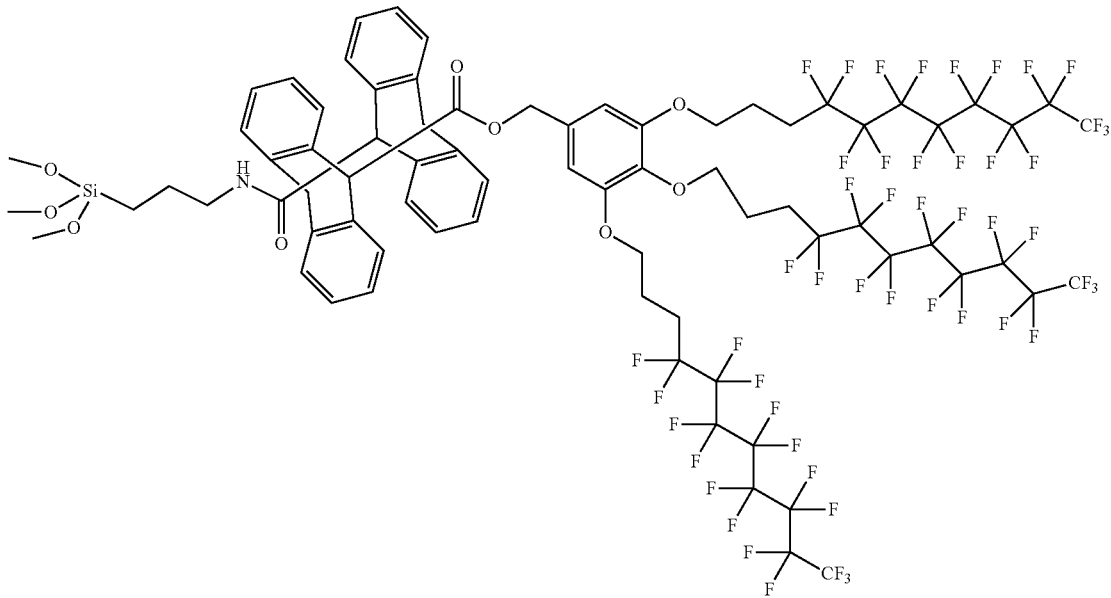

Contact angle of anisole on the substrate thus prepared was measured with a contact angle meter (OCA-30 manufactured by Data Physics Corporation), and consequently it was 25°.

Example 2

First, a glass substrate was cleaned by the following procedure. That is, the substrate was subjected to ultrasonic cleaning using acetone for 30 minutes and then subjected to UV ozone cleaning for 15 minutes.

Next, the compound 1 prepared in Synthesis Example 1 was dissolved in a mixed solvent of equal parts of dehydrated dichloroethylene and dehydrated toluene at a concentration of 4 mM with respect to the solvent to form a solution of the compound 1. The glass substrate subjected to ultrasonic cleaning was immersed in the solution of the compound 1 for 20 minutes.

Thereafter, the glass substrate was taken out and dried at 110° C. for 20 minutes in the air with a hot plate. After drying, chloroform was poured over the glass substrate to remove the excess compound 1 and form a film containing the compound 1.

Next, the compound 2 prepared above was dissolved in chloroform at a concentration of 1 mM with respect to chloroform to form a solution of the compound 2. The above-mentioned substrate having the applied compound 1 was immersed in the solution of the compound 2 for 20 minutes. Thereafter, the glass substrate was taken out and naturally dried in the air to form a film containing the compound 2 on the film containing the compound 1.

Next, trifluorotoluene was poured over the whole substrate to remove the unreacted compound 2. When the light irradiation is not carried out, since the film containing the compound 2 is removed and the film containing the compound 1 is present at the surface of a region where the film containing the compound 2 has been removed, the region is a lyophilic region.

Contact angle of anisole on the substrate thus prepared was measured with a contact angle meter (OCA-30 manufactured by Data Physics Corporation), and consequently it was 5°.

The invention claimed is:

1. A compound represented by any one formula selected from the group consisting of:

[Chem. 31]

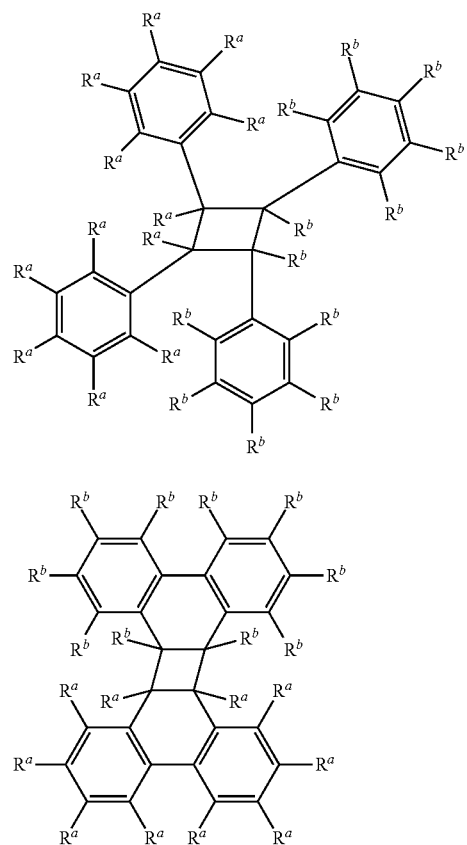

-continued

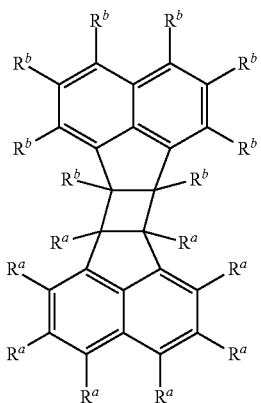

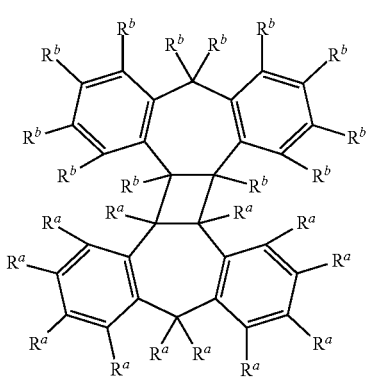

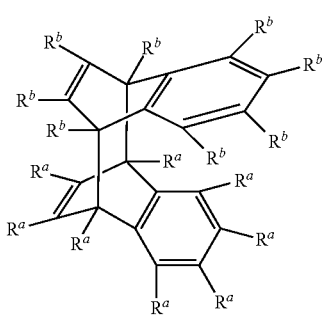

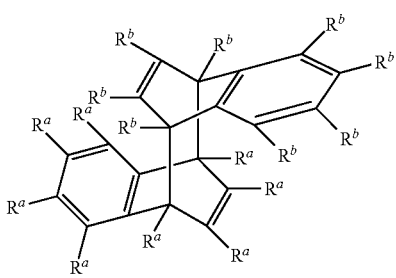

-continued

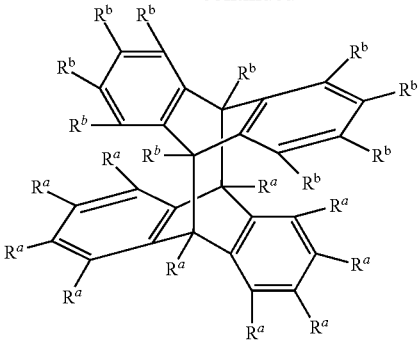

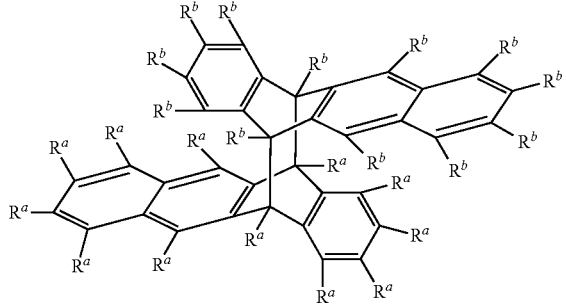

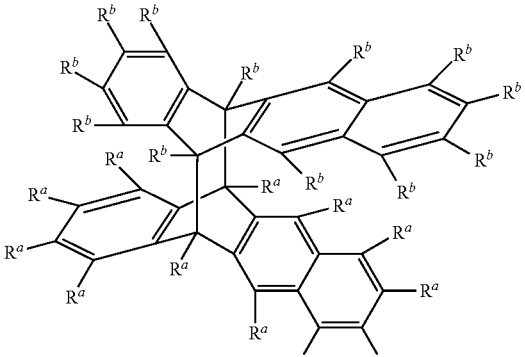

[Chem. 32]

wherein $R^a$s independently represent a hydrogen atom or a substituent, any two adjacent $R^a$s may be coupled with each other to form a ring that is selected from among saturated hydrocarbon rings, unsaturated hydrocarbon rings, aromatic hydrocarbon rings and heterocycles and may have a substituent, at least one of the $R^a$s is a group having lyophilicity, and $R^b$s independently represent a hydrogen atom or a substituent, any two adjacent $R^b$s may be coupled with each other to form a ring that is selected from among saturated hydrocarbon rings, unsaturated hydrocarbon rings, aromatic hydrocarbon rings and heterocycles and may have a substituent, at least one of the $R^b$s is a group having liquid-repellency.

2. The compound according to claim 1, wherein the group having lyophilicity is a group represented by formula (1-3):

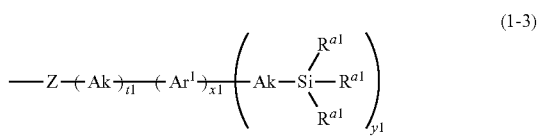

(1-3)

wherein Z represents —C(=O)O—, —OC(=O)—, —OC(=O)O—, —C(=O)—, —N(R$^c$)—, —C(=O)N $(R^c)$—, —N($R^c$)C(=O)—, —N($R^c$)C(=O)N($R^c$)—, -Ak-C(=O)O—, -Ak-OC(=O)—, -Ak-OC(=O)O—, -Ak-C(=O)—, -Ak-N($R^c$)—, -Ak-C(=O)N($R^c$)—, -Ak-N($R^c$)C(=O)—, -Ak-N($R^c$)C(=O)N($R^c$)—, —O—, —S— or -Ak-, $Ar^1$ represents an aromatic hydrocarbon group having a valence of (1+y1) or a heterocyclic group having a valence of (1+y1), Ak represents an alkylene group having 1 to 12 carbon atoms, $R^{a1}$ represents a hydrogen atom, a halogen atom, a hydroxyl group, an alkoxy group or an alkyl group, $R^c$ represents a hydrogen atom or a substituent, and where there are a plurality of $R^c$s, these $R^c$s may be the same or different, t1 represents 0 or 1, x1 represents 0 or 1, and y1 represents an integer of 1 or more, the plurality of $R^{a1}$s may be the same or different, and where there are a plurality of Aks, these Aks may be the same or different.

3. The compound according to claim 1, wherein the group having liquid-repellency is a group represented by the following formula:

[Chem. 7]

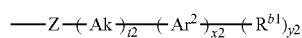

wherein Z represents —C(=O)O—, —OC(=O)—, —OC(=O)O—, —C(=O)—, —N($R^c$)—, —C(=O)N($R^c$)—, —N($R^c$)C(=O)—, —N($R^c$)C(=O)N($R^c$)—, -Ak-C(=O)O—, -Ak-OC(=O)—, -Ak-OC(=O)O—, -Ak-C(=O)—, -Ak-N($R^c$)—, -Ak-C(=O)N($R^c$)—, -Ak-N($R^c$)C(=O)—, -Ak-N($R^c$)C(=O)N($R^c$)—, —O—, —S— or -Ak-, Ak represents an alkylene group having 1 to 12 carbon atoms, $R^c$ represents a hydrogen atom or a substituent, and where there are a plurality of $R^c$s, these $R^c$s may be the same or different, $Ar^2$ represents an aromatic hydrocarbon group having a valence of (1+y2) or a heterocyclic group having a valence of (1+y2), $R^{b1}$ represents a monovalent organic group containing a fluorine atom, t2 represents 0 or 1, x2 represents 0 or 1, y2 represents an integer of 1 or more, and where there are a plurality of $R^{b1}$s, these $R^{b1}$s may be the same or different.

4. The compound according to claim 3, wherein the group having liquid-repellency is a group represented by the following formula:

[Chem. 8]

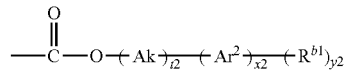

wherein $Ar^2$, $R^{b1}$, Ak, t2, x2 and y2 respectively represent the same meanings as those described above.

5. The compound according to claim 4, wherein the group having liquid-repellency is a group represented by the following formula:

[Chem. 9]

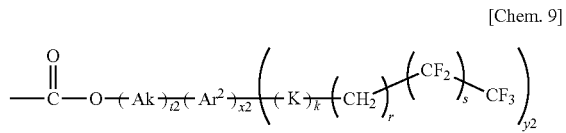

wherein $Ar^2$, Ak, t2, x2 and y2 respectively represent the same meanings as those described above, K represents —O—, —S—, —NH— or —NR—, R represents an alkyl group or an aryl group, k represents 0 or 1, r represents an integer of 0 to 6, s represents an integer of 0 to 16, and where there are a plurality of k's, these k's may be the same or different, where there are a plurality of r's, these r's may be the same or different, and where there are a plurality of s's, these s's may be the same or different.

* * * * *